United States Patent
Limem et al.

(10) Patent No.: US 12,156,802 B2
(45) Date of Patent: Dec. 3, 2024

(54) BREAST RECONSTRUCTION IMPLANT

(71) Applicant: Tepha, Inc., Lexington, MA (US)

(72) Inventors: Skander Limem, Lynnfield, MA (US); Kemal Sariibrahimoglu, Waltham, MA (US); Timothy John Butler, Pelham, NH (US); German Oswaldo Hohl Lopez, East Boston, MA (US); Simon F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 374 days.

(21) Appl. No.: 17/689,538

(22) Filed: Mar. 8, 2022

(65) Prior Publication Data

US 2022/0287820 A1     Sep. 15, 2022

Related U.S. Application Data

(60) Provisional application No. 63/159,914, filed on Mar. 11, 2021.

(51) Int. Cl.
*A61F 2/12*     (2006.01)
*A61F 2/30*     (2006.01)

(52) U.S. Cl.
CPC ...... *A61F 2/12* (2013.01); *A61F 2002/30593* (2013.01); *A61F 2210/0004* (2013.01);
(Continued)

(58) Field of Classification Search
CPC .............. A61F 2/12; A61F 2002/30593; A61F 2230/0023; A61F 2240/002
See application file for complete search history.

(56) References Cited

U.S. PATENT DOCUMENTS 5,121,329 A    6/1992   Crump
5,811,272 A    9/1998   Snell et al.
(Continued)

FOREIGN PATENT DOCUMENTS

CN     205 112 420 U     3/2016
EP     2 258 742 A1     12/2010
(Continued)

OTHER PUBLICATIONS

International Search Report and Written Opinion mailed Jan. 22, 2020 in connection with International Application No. PCT/US2019/036522.
(Continued)

*Primary Examiner* — Suzette J Gherbi
(74) *Attorney, Agent, or Firm* — Wolf, Greenfield & Sacks, P.C.

(57) ABSTRACT

Absorbable implants can be used to create volume and shape in the breast of a patient with regenerated tissue. The implants comprise scaffolds formed from layers of parallel filaments. The layers of filaments can be stacked and bonded together to form scaffolds with porous crisscross arrangements of filaments. The implant's scaffolds may be coated or filled with cells and tissues, including autologous fat graft, and/or a vascular pedicle may be inserted into the implant. The implants are particularly suitable for use in plastic surgery procedures, for example, to regenerate or augment breast tissue following mastectomy or in mastopexy procedures, and can provide an alternative to the use of permanent breast implants in these procedures.

29 Claims, 13 Drawing Sheets

(52) U.S. Cl.
CPC .............. *A61F 2210/0076* (2013.01); *A61F 2230/0023* (2013.01); *A61F 2240/002* (2013.01)

(56) References Cited

U.S. PATENT DOCUMENTS

| | | | |
|---|---|---|---|
| 6,245,537 B1 | 6/2001 | Williams et al. |
| 6,316,262 B1 | 11/2001 | Huisman et al. |
| 6,323,010 B1 | 11/2001 | Skraly et al. |
| 6,548,569 B1 | 4/2003 | Williams et al. |
| 6,555,123 B2 | 4/2003 | Williams et al. |
| 6,585,994 B2 | 7/2003 | Williams et al. |
| 6,610,764 B1 | 8/2003 | Martin et al. |
| 6,623,748 B2 | 9/2003 | Clokie |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,878,758 B2 | 4/2005 | Martin et al. |
| 7,025,980 B1 | 4/2006 | Williams et al. |
| 7,179,883 B2 | 2/2007 | Williams et al. |
| 7,244,442 B2 | 7/2007 | Williams et al. |
| 7,268,205 B2 | 9/2007 | Williams et al. |
| 7,553,923 B2 | 6/2009 | Williams et al. |
| 7,618,448 B2 | 11/2009 | Schmitz et al. |
| 7,641,825 B2 | 1/2010 | Rizk |
| 8,016,883 B2 | 9/2011 | Coleman et al. |
| 8,034,270 B2 | 10/2011 | Martin et al. |
| 8,039,237 B2 | 10/2011 | Martin et al. |
| 8,231,889 B2 | 7/2012 | Williams et al. |
| 8,287,909 B2 | 10/2012 | Martin et al. |
| 8,747,468 B2 | 6/2014 | Martin et al. |
| 9,162,010 B2 | 10/2015 | Lenarz et al. |
| 9,277,986 B2 | 3/2016 | Moses et al. |
| 9,290,612 B2 | 3/2016 | Martin et al. |
| 9,445,930 B2 | 9/2016 | Chen et al. |
| 9,457,127 B2 | 10/2016 | Martin et al. |
| 9,480,780 B2 | 11/2016 | Martin et al. |
| 9,511,169 B2 | 12/2016 | Guo et al. |
| 9,532,867 B2 | 1/2017 | Felix et al. |
| 9,555,155 B2 | 1/2017 | Ganatra et al. |
| 10,064,726 B1 | 9/2018 | Wei |
| 10,709,539 B2 | 7/2020 | Mathisen |
| 10,722,336 B2 | 7/2020 | Mathisen et al. |
| 10,799,336 B2 | 10/2020 | Hutmacher et al. |
| 2006/0051394 A1 | 3/2006 | Moore et al. |
| 2013/0261736 A1 | 10/2013 | Kleiner |
| 2014/0222161 A1 | 8/2014 | Mathisen |
| 2015/0265438 A1 | 9/2015 | Hossainy et al. |
| 2016/0172094 A1 | 6/2016 | Yeom et al. |
| 2017/0123407 A1 | 5/2017 | Shiihara |
| 2018/0049858 A1 | 2/2018 | Tao et al. |
| 2018/0206978 A1 | 7/2018 | Rehnke |
| 2018/0236713 A1 | 8/2018 | Robert |
| 2018/0280145 A1 | 10/2018 | Jones et al. |
| 2019/0247180 A1 | 8/2019 | Limem et al. |
| 2020/0107921 A1 | 4/2020 | Mathisen et al. |
| 2020/0179570 A1 | 6/2020 | Heschel et al. |
| 2020/0261202 A1 | 8/2020 | Mathisen et al. |
| 2020/0375715 A1 | 12/2020 | Egnelov |
| 2020/0375726 A1* | 12/2020 | Limem ............... A61F 2/12 |
| 2021/0153997 A1* | 5/2021 | Limem ............... A61F 2/12 |
| 2021/0369912 A1* | 12/2021 | Toro Estrella ......... B33Y 10/00 |
| 2022/0125575 A1* | 4/2022 | Weems ............... A61F 2/0059 |

FOREIGN PATENT DOCUMENTS

| | | |
|---|---|---|
| EP | 3 238 751 A1 | 11/2017 |
| KR | 2018 0049745 A | 5/2018 |
| WO | WO 99/32536 A1 | 7/1999 |
| WO | WO 2015/164982 A1 | 11/2015 |
| WO | WO 2016/019049 A1 | 2/2016 |
| WO | WO 2016/038083 A1 | 3/2016 |
| WO | WO 2016/058097 A1 | 4/2016 |
| WO | WO 2016/172094 A1 | 10/2016 |
| WO | WO 2017/050837 A1 | 3/2017 |
| WO | WO 2018/078489 A1 | 5/2018 |
| WO | WO 2018/177856 A1 | 10/2018 |
| WO | WO 2019/175901 A1 | 9/2019 |
| WO | WO 2019/217335 A1 | 11/2019 |

OTHER PUBLICATIONS

International Preliminary Report on Patentability mailed Nov. 26, 2020 in connection with International Application No. PCT/US2019/036522.

International Search Report and Written Opinion mailed Aug. 10, 2020 in connection with International Application No. PCT/US2020/030141.

International Preliminary Report on Patentability mailed Dec. 9, 2021 in connection with International Application No. PCT/US2020/030141.

International Search Report and Written Opinion mailed Jun. 3, 2022 in connection with International Application No. PCT/US2022/019228.

Chiulan, et al., Recent advances in 3D printing of aliphatic polyesters, Bioengineering, 5(1):2 (2018):1-18.

Derakhshanfar, et al., 3D bioprinting for biomedical devices and tissue engineering: a review of recent trends and advances, Bioactive Materials, 3:144-156 (2018).

Hori, et al., Chemical synthesis of high molecular weight poly (3-hydroxybutyrate-co-4-hydroxybutyrate), Polymer 36(24):4703-4705 (1995).

Houk, et al., Why δ-Valerolactone Polymerizes and γ-Butyrolactone Does not, J. Org. Chem., 73(7):2674-2678 (2008).

Martin, et al., Medical Applications of Poly-4-hydroxybutyrate: A Strong Flexible Absorbable Biomaterial, Biochem. Eng. J., 16:97-105 (2003).

Moore, et al., Chemosynthesis of bioresorbable poly (γ-butyrolactone) by ring-opening polymerisation: a review, Biomaterials 26:3771-3782 (2005).

Sodian, et al., Application of stereolithography for scaffold fabrication for tissue engineered heart valves, ASAIO Journal, 48:12-16 (2002).

Steinbüchel, et al., Diversity of Bacterial Polyhydroxyalkanoic Acids, FEMS Microbial. Lett., 128:219-228 (1995).

Williams, et al., Applications of PHAs in Medicine and Pharmacy, in Biopolymers, Polyesters, III (4):91-127 (2002).

Zhou et al., Tuning the mechanics of 3D-printed scaffolds by crystal lattice-like structural design for breast tissue engineering, 2020 Biofabrication 12 015023. 18 pages.

* cited by examiner

BREAST RECONSTRUCTION IMPLANT

CROSS REFERENCE TO RELATED APPLICATION

This application claims the benefit of U.S. Provisional Application No. 63/159,914, filed Mar. 11, 2021, which is hereby incorporated by reference in its entirety.

FIELD

Aspects provided herein generally relate to three-dimensional porous implants with compressive modulus suitable for replacing breast tissue. More particularly, the implants are absorbable, and are formed by bonding parallel planes of filaments to each other to provide scaffolds with suitable compressive modulus. The implants are designed to replace or increase the volume of soft tissue when implanted in the breast.

BACKGROUND

Breast reconstruction following mastectomy has become an integral and important part of breast cancer treatment with the surgery providing the patient with both aesthetic and psychosocial benefits. In the US, nearly 65% of breast reconstruction procedures now use a tissue expander to create a pocket for a permanent breast implant in the first step of the procedure. In some patients, a pocket for the breast implant can be formed without the use of a tissue expander. Once a pocket has been created, the tissue expander is removed, and replaced with a permanent breast implant in a second step.

Breast implants can also be used in breast augmentation and mastopexy procedures to augment breast size. In the latter procedure, a breast lift is combined with breast augmentation. Most commonly, the breast implant is placed in a pocket under the breast tissue, but in some cases, it is implanted under the chest wall.

Breast implants differ in dimensions, shape, and surface texture. A wide variety of different dimensions are available allowing the surgeon and patient to select from a range of projections, heights, widths and overall volume. In terms of shape, there are round and anatomically shaped implants, and the surfaces of the implants may be smooth, micro-textured or macro-textured. Generally, round implants have smooth surfaces, whereas anatomically shaped implants have dimpled micro- or macro-textured surfaces.

SUMMARY OF THE INVENTION

In some aspects, implants are provided. In some embodiments, a breast implant may include a porous three-dimensional scaffold, wherein the implant includes a back area for placement on the chest wall of a patient, a front area opposite the back area, the front area comprising a front bottom for placement in the lower pole of the breast, a front top for placement in the upper pole of the breast, and a front intermediate-region for placement under the skin of the patient, wherein the implant has a compressive modulus of 0.1 kPa to 10 MPa, wherein the scaffold comprises at least two adjacent parallel planes of filaments bonded to each other, and wherein the filaments in each plane extend in the same direction.

In some aspects, methods of manufacture are provided. In some embodiments, a method of manufacturing a breast implant is provided, the breast implant including a porous three-dimensional scaffold, wherein the implant includes a back area for placement on the chest wall of a patient, a front area opposite the back area, the front area comprising a front bottom for placement in the lower pole of the breast, a front top for placement in the upper pole of the breast, and a front intermediate-region for placement under the skin of the patient, wherein the implant has a compressive modulus of 0.1 kPa to 10 MPa, and wherein the scaffold comprises at least two adjacent parallel planes of filaments bonded to each other with the filaments in each plane extending in the same direction, wherein the method includes forming a scaffold by one of the following (i) forming at least two parallel planes of filaments from a polymeric composition by 3D printing of the filaments, and (ii) forming at least two parallel planes of filaments from a polymeric composition by melt extrusion deposition printing.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1C:
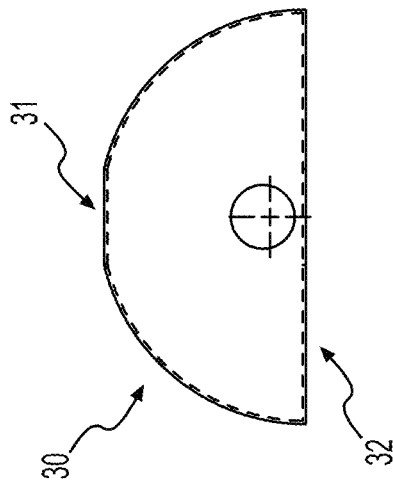
FIG. 1C is a top view of a breast implant scaffold 20 shown in FIG. 1A with a second medial to lateral opening 21 for insertion of a tissue mass.

A growing number of patients considering breast reconstruction and augmentation are however reluctant to have permanent breast implants placed in their breasts. This is particularly the case for women that have had a mastectomy, and are now considering breast reconstruction. Some of these patients do not want to have a permanent foreign body placed in their breasts, and they don't want to run the risk of complications that can develop with permanent breast implants. The complications include a risk of: capsular contraction requiring reoperation, rupture or deflation of the implant, development of anaplastic large cell lymphoma (ALCL), infection, and movement of the implants causing asymmetry of the breasts.

WO2016/038083 to Hutmacher discloses an implant for tissue reconstruction which comprises a scaffold structure that includes a void system for the generation of prevascularized connective tissue with void spaces for cell and/or tissue transplantation. See Abstract Hutmacher.

US2018/0206978 to Rehnke discloses an internal brassiere device made from a pleated scaffold that can be used in breast augmentation patients.

WO2018/078489 to Danze discloses a device to be implanted in a subject's body to form an implant for replacing and/or increasing a volume of soft tissue, the device being of the type including a three-dimensional frame which defines an inner space in said frame. The frame is typically bio-absorbable and includes two side apertures forming a transverse passage for inserting a vascular pedicle; the device further comprises at least two bio-absorbable textile sheets that can be stacked on each other in the inner space of said frame. See Abstract Danze.

US2020/0375726 to Limem discloses implants formed from unit cells suitable for use in breast reconstruction.

WO2019/217335 to Toro Estrella discloses bio-scaffold structures comprising a plurality of connected unit cells, wherein each unit cell includes at least one opening connected to an internal volume.

Notwithstanding the above, the inventors have recognized a need for improved breast implants that, when implanted, can generate new breast tissue with a specific and desirable appearance.

Breast implants described herein assist the surgeon in reconstructing the breast particularly following mastectomy, enhancing the appearance of the breast, augmenting the size of the breast, reconstructing lost or missing breast tissue, enhancing the tissue structure of the breast, increasing the soft tissue volume of the breast, restoring the natural feeling of soft tissue in the breast, and delivering biological and synthetic materials to assist in tissue regeneration, repair, and reconstruction of the breast.

In embodiments, the breast implants are porous, providing scaffolding for tissue ingrowth, and may further comprise cells, collagen, recombinant collagen (e.g., type I collagen, and/or rhCollagen), autologous fat, fat lipoaspirate, or injectable fat. Following implantation, the implant is designed to be invaded by connective tissue and blood vessels, and become well integrated in the breast. In embodiments, the implant may be an adipose tissue engineering scaffold.

In embodiments, the breast implants comprise a porous three-dimensional scaffold formed from at least two adjacent parallel planes of filaments bonded to each other. The filaments in each layer extend in the same direction, and are generally parallel to one another. In some embodiments, the scaffold may be 3D printed. In embodiments, the at least two parallel planes of filaments have the same orientation in adjacent planes or nonadjacent planes within the scaffold. In embodiments, a first parallel plane of filaments is organized in a first geometrical orientation, and a second parallel plane of filaments is arranged in a second geometrical orientation to form a porous scaffold with crisscrossed filaments. In embodiments, the angles between the filaments in the different parallel planes is between 0 and 179 degrees. In embodiments, the scaffold is formed with each subsequent parallel plane of filaments offset from the previous plane of filaments by 18 degrees such that the tenth layer of filaments has the same orientation as the first layer of filaments. In embodiments, the scaffold is formed with each subsequent parallel plane of filaments offset from the previous plane of filaments by 20 degrees such that the ninth layer of filaments has the same orientation as the first layer of filaments. In embodiments, the scaffold is formed with each subsequent parallel plane of filaments offset from the previous plane of filaments by 30 degrees such that the sixth layer of filaments has the same orientation as the first layer of filaments. In embodiments, the scaffold is formed with each subsequent parallel plane of filaments offset from the previous plane of filaments by 36 degrees such that the fifth layer of filaments has the same orientation as the first layer of filaments. In embodiments, the scaffold is formed with each subsequent parallel plane of filaments offset from the previous plane of filaments by 45 degrees such that the fourth layer of filaments has the same orientation as the first layer of filaments. In embodiments, the scaffold is formed with each subsequent parallel plane of filaments offset from the previous plane of filaments by 60 degrees such that the third layer of filaments has the same orientation as the first layer of filaments. In the latter case, the angles between the filaments in the different planes are 0, 60 and 120 degrees, and the filaments are oriented in the scaffold to form pores with a triangular shape.

In embodiments, the implant has a shape and size suitable for use in breast surgery procedures, including breast augmentation, breast reconstruction and mastopexy.

In embodiments, the implant or scaffold comprises pores with an average diameter or average width of 100 to 500 microns.

In embodiments, the planes of filaments present in the scaffold of the breast implant are formed from a polymeric composition. The polymeric composition may have one or more of the following properties: (i) an elongation at break greater than 100%; (ii) an elongation at break greater than 200%; (iii) a melting temperature of 60° C. or higher, (iv) a melting temperature higher than 100° C., (v) a glass transition temperature of less than 0° C., (vi) a glass transition temperature between −55° C. and 0° C., (vii) a tensile modulus less than 300 MPa, and (viii) a tensile strength higher than 25 MPa.

In embodiments, the filaments have an average diameter or average width of 50 μm to 5 mm.

In embodiments, the filaments have one or more of the following properties: (i) a breaking load of 0.1 to 200 N; (ii) an elongation at break of 10-1,000%, and/or 25-500%, and (iii) an elastic modulus of 0.05 to 1,000 MPa or 0.1 to 200 MPa.

In embodiments, filaments of the implants are formed with surface roughness (Ra). Surface roughness promotes cell attachment and tissue formation on the implants. Surface roughness also promotes attachment of the implant to neighboring tissues, encourages tissue in-growth, and helps to prevent movement of the device after implantation. In embodiments, the implant comprises filaments having a surface roughness of 0.02 to 75 microns, 0.1 to 50 or 0.5 to 30 microns, and/or 5 to 30 microns. In embodiments, filaments of the implant are 3D printed with these surface roughness values.

In embodiments, the infill density of filaments in the scaffold is between 1% and 60%, and/or between 5% and 25%.

In embodiments, the breast implant has a compressive modulus of 0.1 kPa to 10 MPa, 0.3 kPa to 1 MPa, and/or 3 kPa to 200 kPa. The compressive modulus allows the implant to be compressed when a compressive force is applied, and recover from compression when the compressive force is removed. The breast implant may be engineered so that the breast feels soft to the touch, similar to a natural breast. In embodiments, the breast implant allows the surgeon to restore or augment breast mass while maintaining or restoring the tactile sensation of the breast.

In embodiments, the breast implant has a loss modulus of 0.1 kPa to 5 MPa, 0.3 kPa to 1 MPa, and/or 0.3 kPa to 100 kPa.

In embodiments, the breast implant may have a compression resilience of 1 to 80%. In some embodiments, the breast implant may have a compression resilience of at least 50%, 70%, 75%, 80%, 90% and/or any other suitable percentage.

In embodiments, the breast implant may be configured to recover at least 50%, 70%, 75%, 90%, and/or any other suitable proportion or more of its original volume upon the application and subsequent removal of a compressive force. In some embodiments, the breast implant may recover at least 50%, 70%, 75%, 90%, and/or any other suitable proportion of its original volume upon the application and subsequent removal of a compressive force.

In embodiments, the implants have anisotropic properties meaning that the implants have different properties in different directions. The implants may have a first compression modulus in one direction, and a second different compression modulus in a second direction.

In embodiments, the breast implant comprises a back area for placement on the chest wall of the patient, a front area opposite the back area, the front area comprising a front bottom for placement in the lower pole of the breast, a front top for placement in the upper pole of the breast, and a front intermediate-region for placement under the skin of the patient.

In embodiments, the breast implant has a longitudinal axis defined by the axis between the back area and front area of the implant.

In embodiments, the front bottom area of the breast implant comprises a convex exterior surface. The convex exterior surface is sized and shaped to enhance the profile of the lower pole of the breast, and, in some embodiments, approximates the anatomical feature of the lower pole of the breast.

In embodiments, the breast implant further comprises an opening for insertion of tissue into the implant. In embodiments, the opening is located on the back area of the implant. In embodiments, the opening is located on the back area of the implant, and has a longitudinal axis between the back and front areas of the implant. In embodiments, the implant may have an opening that is a hollow core defining a longitudinal axis between the back and front areas of the implant.

In embodiments, the implants may comprise two or more openings to allow the insertion of multiple vascular pedicles, or other masses of tissue into the implant.

In embodiments, the scaffold further comprises a plurality of hollow channels. In embodiments, the hollow channels are straight. In embodiments, the hollow channels are present between the back and front areas of the implant. In embodiments, the hollow channels have an average diameter greater than 100 µm.

In embodiments, the implant further comprises one or more anchors, fasteners or tabs to fixate the implant in the breast.

In embodiments, the implant further comprises an exterior shell or coating at least partly surrounding the parallel planes of filaments. In embodiments, the shell has an outer surface and an inner surface that surrounds an interior volume of said shell. In embodiments, the shell or coating comprises a foam, an open cell foam, a collagen coating, or a coating comprising poly-4-hydroxybutyrate or copolymer thereof or poly(butylene succinate) or copolymer thereof.

The shell may have pores, and may have an infill density in the range of 30-100%. In embodiments, the back of the implant is shell-less and the front has a shell.

In embodiments, the implant is shell-less, and optionally the perimeter edges are treated, for example, to remove barbs and make generally smoother. The edges may be treated by, for example, trimming or heat treating.

In embodiments, the implant further comprises one or more of the following: autologous fat, fat lipoaspirate, injectable fat, adipose cells, fibroblast cells, stem cells, gels, hydrogels, hyaluronic acid, collagen, recombinant collagen (e.g., type I and/or rhCollagen), antimicrobial, antibiotic, bioactive agent, and diagnostic device.

In embodiments, the implants can be easily engineered into any shape, for example, shapes that provide a specific and desirable appearance of the breast. In embodiments, the implant has a shape designed to provide the breast with a desirable anatomical shape. In embodiments, the implant has a dome-like shape.

In embodiments, the implant can be temporarily deformed for implantation. In embodiments, the implant can be delivered to the breast in a minimally invasive manner.

In embodiments, the implant or scaffold comprises an absorbable polymer. In embodiments, the absorbable polymer comprises, or is prepared from, one or more monomers selected from the group: glycolide, lactide, glycolic acid, lactic acid, 1,4-dioxanone, trimethylene carbonate, 3-hydroxybutyric acid, 3-hydroxybutyrate, 4-hydroxybutyric acid, 4-hydroxybutyrate, ε-caprolactone, 1,4-butanediol, 1,3-propane diol, ethylene glycol, glutaric acid, malic acid, malonic acid, oxalic acid, succinic aid, and adipic acid.

In embodiments, the implant or scaffold comprises poly-4-hydroxybutyrate (P4HB) and copolymers thereof, or poly(butylene succinate) (PBS) and copolymers thereof. In embodiments, the P4HB and PBS polymers, and copolymers thereof, are not crosslinked. In embodiments, the PBS polymer and copolymers may further comprise one or more of the following: branching agent, cross-linking agent, chain extender agent, and reactive blending agent. The PBS and P4HB polymers and copolymers may be isotopically enriched.

In embodiments, the polymers used to prepare the implants have weight average molecular weights of 50 to 1,000 kDa, 90 to 600 kDa, and/or from 200 to 450 kDa relative to polystyrene determined by GPC.

In embodiments, the scaffold is made of a material that can hold micro-globules of lipo-suctioned fat in place, and prevent pooling of fat which can lead to necrosis.

In embodiments, the scaffold comprises a lipophilic polymer to allow for better adsorption of fat, including fat harvested from a patient, for example, by liposuction.

In embodiments, the scaffold comprises a hydrophobic polymer to allow for better absorption of fat, wherein the hydrophobic polymer has a water contact angle greater than 90 degrees.

In embodiments, the breast implant is absorbable. The implants may be formed of a polymeric material with a predictable rate of degradation, and a predictable strength retention in vivo. When the implants are absorbable, degradation of the implant can allow further invasion of the implant with tissue, blood vessels or a combination thereof, and this process can continue until the implant is completely absorbed.

In embodiments, the implant retains strength long enough to allow the shape of the breast at the implant site to be transitioned from the implant to new tissue. The implant needs to maintain its shape for a prolonged period in order to direct re-modeling of the patient's tissue. In some embodiments, the implant may provide support of the breast until support is transitioned from the implant to new tissue. In some embodiments, minimal loss of support for the shape of the breast occurs during this transition period. The shape of the breast implant is maintained for a prolonged period in order to direct tissue in-growth into the implant, and produce the desired breast shape.

In embodiments, the implant is formed using a process wherein the parallel planes of filaments of the scaffold are formed by 3D printing. In embodiments, the parallel planes of filaments of the scaffold are formed by melt extrusion deposition printing.

In embodiments, methods are provided for manufacturing implants comprising a porous three-dimensional scaffold with a compressive modulus of 0.1 kPa to 10 MPa, 0.3 kPa to 1 MPa, and/or 3 kPa to 200 kPa, at least two parallel planes of filaments, a back area for placement on the chest wall of a patient, a front area opposite the back area, the front area comprising a front bottom for placement in the lower pole of the breast, a front top for placement in the upper pole of the breast, and a front intermediate-region for placement under the skin of the patient, wherein the front bottom area comprises a convex surface, the method comprising forming at least parallel planes of filaments from a polymeric composition by 3D printing of the filaments, and/or by melt extrusion deposition. In embodiments, the methods of manufacturing the implants comprise forming the parallel planes of filaments by 3D printing from a polymeric composition selected from a polymer or copolymer comprising, or prepared from, one or more of the following monomers: glycolide, lactide, glycolic acid, lactic acid, 1,4-dioxanone, trimethylene carbonate, 3-hydroxybutyric acid, 3-hydroxybutyrate, 4-hydroxybutyric acid, 4-hydroxybutyrate, ε-caprolactone, 1,4-butanediol, 1,3-propane diol, ethylene glycol, glutaric acid, malic acid, malonic acid, oxalic acid, succinic aid, and adipic acid, or wherein the polymeric composition comprises poly-4-hydroxybutyrate or copolymer thereof, or poly(butylene succinate) or copolymer thereof. In embodiments, the methods of manufacturing the implants comprise forming the filaments of the scaffold from a polymer with one or more of the following properties: (i) an elongation at break greater than 100%; (ii) an elongation at break greater than 200%; (iii) a melting temperature of 60° C. or higher, (iv) a melting temperature higher than 100° C., (v) a glass transition temperature of less than 0° C., (vi) a glass transition temperature between −55° C. and 0° C., (vii) a tensile modulus less than 300 MPa, and (viii) a tensile strength higher than 25 MPa. In some embodiments, the scaffold of the implant is made from P4HB, PBS, P4HB copolymers or PBS copolymers, by 3D printing. In embodiments, the method of manufacturing the implant comprises forming the filaments of the scaffold by 3D printing with one or more of the following properties: (i) an elongation at break greater than 100%; (ii) an elongation at break greater than 200%; (iii) a melting temperature of 60° C. or higher, (iv) a melting temperature higher than 100° C., (v) a glass transition temperature of less than 0° C., (vi) a glass transition temperature between −55° C. and 0° C., (vii) a tensile modulus less than 300 MPa, and (viii) a tensile strength higher than 25 MPa. In embodiments, methods of manufacturing the implants comprise 3D printing the scaffold, and adding one or more of the following components: autologous fat, fat lipoaspirate, injectable fat, adipose cells, fibroblast cells, stem cells, gel, hydrogel, hyaluronic acid, collagen, recombinant collagen (e.g., type I and/or rhCollagen), antimicrobial, antibiotic, bioactive agent, and diagnostic device. In embodiments, these components are added to the scaffold by coating, spraying, immersion or injection.

In embodiments, the implant has a pre-determined three-dimensional shape that can be implanted subcutaneously, between the skin and the breast mound or chest wall of the breast. The breast implant may be implanted in the sub-glandular, sub-pectoral, or subfascial positions. The implant design allows the surgeon to easily control the volumetric ratios of the upper and lower poles of the breast, the extent of protrusion of the breast from the chest wall, and the curvatures of the upper and lower poles of the breast.

In embodiments, the implant serves to provide the surgeon with a means to deliver cells, stem cells, differentiated cells, fat cells, muscle cells, platelets, tissue, pedicles, vascular pedicles, tissue masses, lipoaspirate, extracellular adipose matrix proteins, gels, hydrogels, hyaluronic acid, collagen, recombinant collagen (e.g., type I and/or rhCollagen), bioactive agents, drugs, antibiotics, and other materials to the implant site. In some embodiments, the cells and tissues delivered by the implants, or coated or injected into the implants, are autologous. The implants may be used for autologous fat transfer. The implants may comprise bioactive agents to stimulate cell in-growth, including growth factors, cell adhesion factors, cellular differentiating factors, cellular recruiting factors, cell receptors, cell-binding factors, cell signaling molecules, such as cytokines, and molecules to promote cell migration, cell division, cell proliferation and extracellular matrix deposition.

In embodiments, the implants can be implanted to replace and/or increase a soft tissue volume or a tissue mass. In embodiments, the implants may further comprise a growth chamber for cells and tissues.

In embodiments, the implants have an endotoxin content of less than 20 endotoxin units per implant.

In embodiments, the implants are sterilized implants. The implants can be sterilized by a range of techniques including without limitation ethylene oxide, electron beam, or gamma-irradiation.

In embodiments, methods are provided for implanting the implants in the breast of a patient. In embodiments, the methods of implantation of the implants comprise: (i) making at least one incision to gain access to the breast tissue of the patient, (ii) separating the skin and subcutaneous fascia from the breast mound of the breast, (iii) positioning the implant sub-glandular, sub-pectoral, or subfascial (iv) securing the implant to nearby tissue, and (v) closing the incisions in the breast. In embodiments, the method of implanting the implants in the breast further comprise coating on the implant, or adding to the implant, one or more of the following components on one or more occasions either prior to implanting the implant in the breast or after implanting the implant in the breast: autologous fat, fat lipoaspirate, injectable fat, adipose cells, fibroblast cells, stem cells, gel, hydrogel, hyaluronic acid or derivative thereof, collagen, recombinant collagen, antimicrobial, antibiotic, and a bioactive agent. In embodiments, the components are added to the implant by injection, spraying, immersion or coating, and/or injection of the components onto or into the scaffold of the implant. In embodiments, the implant is coated with autologous tissue from the patient prior to implantation, during implantation, or after implantation, or any combination thereof. In embodiments, the method of implantation comprises implanting an implant with an opening sized for insertion of tissue into the implant, and inserting tissue or pedicle, such as a vascular pedicle, a vascular pedicle perforator, and/or a pedicle from the small pectoral muscle with a perforator, into the opening of the implant during implantation of the implant. In embodiments, the method of implantation comprises dissecting a pedicle from the patient's small pectoral muscle, with a perforator, and inserting the pedicle in an opening in the implant that is sized to receive the pedicle. In embodiments, the surgeon may insert a pedicle or other tissue mass in the implant prior to, or after, implantation of the implant in a patient. The breast implant can be used in patients that have: (i) undergone mastectomy, (ii) undergone breast lift and have need of an augmentation, (iii) undergone breast reduction and need support and lift of the reduced breast, (iv) undergone prior silicone or saline breast implant breast surgery, and desire that the silicone or saline implant is removed and that there is subsequent reconstruction of the breast to produce a youthful appearance but with a fuller breast and larger size. The implant may also be used in patients that want the feeling of natural breast tissue restored to the breast after removal of their breast tissue. The implant can be used to increase projection of the breast from the chest, and in combination with fat grafting to add volume to the breast.

These advantages as well as other objects and advantages of the present invention will become apparent from the description to follow, together with the accompanying drawings.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

To further assist in understanding the following definitions are set forth below. However, it is also to be appreciated that unless defined otherwise as described herein, all technical and scientific terms used herein have the same meaning as commonly understood by one of ordinary skill in the art to which this invention belongs.

I. Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes.

"Bioactive agent" as generally used herein refers to therapeutic, prophylactic or diagnostic agents, agents that promote healing and the regeneration of host tissue, and also therapeutic agents that prevent, inhibit or eliminate infection. "Agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Compressive modulus" as used herein is measured with a mechanical testing bench (QTest™/1L, MTS, USA) at a cross-head speed of 20 mm min$^{-1}$. Samples are preloaded (10% of the initial compressive load) to engage the load and compressed up to 1 mm (20%) of their original height. Clinically relevant cyclic load is repeated 10 times and compressive modulus is calculated based on secondary cyclic load due to the artifact caused by a take up of slack, and alignment or seating of the specimen. Compressive modulus may also be measured using ASTM standards ASTM D1621-16 or ASTM D695-15.

"Compression resilience" as used herein is calculated as the work done during compression recovery divided by the work done during compression multiplied by 100.

"Copolymers of poly-4-hydroxybutyrate" as generally used herein means any polymer containing 4-hydroxybutyrate with one or more different hydroxy acid units. The copolymers may be isotopically enriched.

"Copolymers of poly(butylene succinate)" as generally used herein means any polymer containing 1,4-butanediol and succinic acid units, and one or more different diol or diacid units. The copolymers may include one or more of the following: branching agent, cross-linking agent, chain extender agent, and reactive blending agent. The copolymers may be isotopically enriched.

"Endotoxin content" as generally used herein refers to the amount of endotoxin present in an implant or sample, and is determined by the limulus amebocyte lysate (LAL) assay.

"Infill density" as used herein is the ratio of volume occupied by 3D printed material in an implant scaffold divided by the total volume of the 3D printed scaffold expressed as a percentage.

"Molecular weight" as generally used herein, unless otherwise specified, refers to the weight average molecular weight (Mw), not the number average molecular weight (Mn), and is measured by GPC relative to polystyrene.

"Poly(butylene succinate)" mean a polymer containing 1,4-butanediol units and succinic acid units. The polymer may include one or more of the following: branching agent, cross-linking agent, chain extender agent, and reactive blending agent. The polymer may be isotopically enriched.

"Poly(butylene succinate) and copolymers" includes polymers and copolymers prepared with one or more of the following: chain extenders, coupling agents, cross-linking agents and branching agents.

"Poly-4-hydroxybutyrate" as generally used herein means a homopolymer containing 4-hydroxybutyrate units. It can be referred to herein as P4HB or TephaFLEX® biomaterial (manufactured by Tepha, Inc., Lexington, MA). The polymers may be isotopically enriched.

"Subfascial" as used herein means under the connective tissue sheath (the outer fascia) of the pectoral muscle, but above the pectoral muscle.

"Soft tissue" as used herein means body tissue that is not hardened or calcified. Soft tissue excludes hard tissues such as bone and tooth enamel.

"Strength retention" refers to the amount of time that a material maintains a particular mechanical property following implantation into a human or animal. For example, if the tensile strength of a resorbable fiber or strut decreases by half over 3 months when implanted into an animal, the fiber or strut's strength retention at 3 months would be 50%.

"Sub-glandular" as used herein means under the breast tissue and above the pectoral muscle.

"Sub-pectoral" as used herein means at least partially under the pectoral muscle.

"Surface roughness" (Ra) as used herein is the arithmetic average of the absolute values of the profile height deviations from a mean line, recorded within an evaluation length.

II. Materials for Preparing Implants

In embodiments, the implants can be used to reshape the breast, fill voids in the breast, lift the breast, and augment the breast. The implants are soft tissue implants meaning that they can be used for soft tissue regeneration, augmentation, repair, reinforcement, and reconstruction. The implants can eliminate the need to use permanent breast implants during mastectomy, mastopexy and breast augmentation procedures. The implants are biocompatible, and may be replaced in vivo by the patient's tissue as the implants degrade. The implants are particularly suitable for augmentation of the breast, especially soft tissues of the breast. The implants may have a compressive modulus that allows the implant to temporarily deform under a compressive force, recover their shape from compression when the force is removed, and have a feel similar to breast tissue. Optionally, the implants can be coated or filled with autologous tissue, autologous fat, fat lipoaspirate, injectable fat, adipose cells, fibroblast cells, and stem cells prior to implantation, during implantation, or post-implantation. The implants may further comprise one or more openings or passages, including one or more transverse passages, to allow insertion of a vascular pedicle or other tissue mass in the implant.

A. Polymers for Preparing Implants

In embodiments, the implants contain scaffolds that are formed from at least two parallel layers of filaments bonded together. In embodiments, the filaments in a first layer have a first orientation, and the filaments in a second layer have a second orientation that is different to the first orientation. In embodiments, the filaments in the first and second layers of the scaffold are crisscrossed. In embodiments, the scaffold may comprise additional layers of filaments with different orientations to the first and second orientations of filaments. In embodiments, the adjacent layers of filaments are bonded to each other at multiple points where they crisscross. In embodiments, pores are formed between the filaments of the scaffold. The dimensions of the pores are dependent upon the number and direction of the filaments in the scaffold, the spacing of the filaments, and the size and shape of the filaments. A scaffold may comprise two or more parallel layers of filaments bonded together, including, but not limited to 20, 30, 40, 50 or more layers of filaments. The scaffolds may optionally comprise other features, such as one or more openings or passages, including one or more transverse passages.

The scaffold of the implant may comprise permanent materials, such as non-degradable thermoplastic polymers, including polymers and copolymers of ethylene and propylene, including ultra-high molecular weight polyethylene, ultra-high molecular weight polypropylene, nylon, polyesters such as poly(ethylene terephthalate), poly(tetrafluoroethylene), polyurethanes, poly(ether-urethanes), poly(methylmethacrylate), polyether ether ketone, polyolefins, and poly(ethylene oxide). However, the scaffold of the implant may include absorbable materials, thermoplastic or polymeric absorbable materials, and/or the implant and the implant's scaffold may be made completely from absorbable materials.

In some embodiments, the implant's scaffold may be made from one or more absorbable polymers or copolymers, absorbable thermoplastic polymers and copolymers, and/or absorbable thermoplastic polyesters. The implant's scaffold may, for example, be prepared from polymers including, but not limited to, polymers comprising glycolic acid, glycolide, lactic acid, lactide, 1,4-dioxanone, trimethylene carbonate, 3-hydroxybutyric acid, 4-hydroxybutyrate, 3-hydroxyhexanoate, 3-hydroxyoctanoate, ε-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly (alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly (lactide-co-glycolide), or polycaprolactone and copolymers thereof, including random copolymers and block copolymers thereof.

In some embodiments, the scaffold of the implant is prepared from an absorbable polymer or copolymer that will be substantially resorbed after implantation within a 1 to 24-month timeframe, and/or a 3 to 18-month timeframe, and retain some residual strength for at least 2 weeks to 6 months.

Blends of polymers and copolymers, absorbable polymers, may also be used to prepare the implant's scaffold. Blends of absorbable polymers may be prepared from absorbable polymers including, but not limited to, polymers comprising glycolic acid, glycolide, lactic acid, lactide, 1,4-dioxanone, trimethylene carbonate, 3-hydroxybutyric acid, 4-hydroxybutyrate, ε-caprolactone, 1,4-butanediol, 1,3-propane diol, ethylene glycol, glutaric acid, malonic acid, oxalic acid, succinic aid, adipic acid, or copolymers thereof.

In some embodiments, poly-4-hydroxybutyrate (Tepha's P4HB™ polymer, Lexington, MA) or a copolymer thereof is used to make the implant's scaffold. Copolymers include P4HB with another hydroxy acid, such as 3-hydroxybutyrate, and P4HB with glycolic acid or lactic acid monomer. Poly-4-hydroxybutyrate is a strong, pliable thermoplastic polyester that is biocompatible and resorbable (Williams, et al. Poly-4-hydroxybutyrate (P4HB): a new generation of resorbable medical devices for tissue repair and regeneration, *Biomed. Tech.* 58 (5):439-452 (2013)). Upon implantation, P4HB hydrolyzes to its monomer, and the monomer is metabolized via the Krebs cycle to carbon dioxide and water. In some embodiments, the P4HB homopolymer and copolymers thereof may have a weight average molecular weight, Mw, within the range of 50 kDa to 1,200 kDa (by GPC relative to polystyrene), from 100 kDa to 600 kDa, and/or 200 kDa to 450 kDa. A weight average molecular weight of the polymer of 50 kDa or higher may be employed for processing and mechanical properties.

In some embodiments, the scaffold of the implant may be prepared from a polymer comprising at least a diol and a diacid. In some embodiments, the polymer used to prepare the scaffold may be poly(butylene succinate) (PBS) wherein the diol is 1,4-butanediol and the diacid is succinic acid. The poly(butylene succinate) polymer may be a copolymer with other diols, other diacids or a combination thereof. For example, the polymer may be a poly(butylene succinate) copolymer that further comprises one or more of the following: 1,3-propanediol, ethylene glycol, 1,5-pentanediol, glutaric acid, adipic acid, terephthalic acid, malonic acid, methylsuccinic acid, dimethylsuccinic acid, and oxalic acid. Non-limiting examples of copolymers may include: poly (butylene succinate-co-adipate), poly(butylene succinate-co-terephthalate), poly(butylene succinate-co-butylene methylsuccinate), poly(butylene succinate-co-butylene dimethylsuccinate), poly(butylene succinate-co-ethylene succinate) and poly(butylene succinate-co-propylene succinate). The poly(butylene succinate) polymer or copolymer may also further comprise one or more of the following: chain extender, coupling agent, cross-linking agent and branching agent. For example, poly(butylene succinate) or copolymer thereof may be branched or cross-linked by adding one or more of the following agents: malic acid, trimethylol propane, glycerol, trimesic acid, citric acid, glycerol propoxylate, and tartaric acid. Agents for branching or crosslinking the poly(butylene succinate) polymer or copolymer thereof may be hydroxycarboxylic acid units. The hydroxycarboxylic acid unit may have two carboxylic groups and one hydroxyl group, two hydroxyl groups and one carboxyl group, three carboxyl groups and one hydroxyl group, or two hydroxyl groups and two carboxyl groups. In some embodiments, the implant's scaffold may be prepared from poly(butylene succinate) comprising malic acid as a branching or cross-linking agent. This polymer may be referred to as poly(butylene succinate) cross-linked with malic acid, succinic acid-1,4-butanediol-malic acid copolyester, or poly (1,4-butylene glycol-co-succinic acid), cross-linked with malic acid. It should be understood that references to malic acid and other cross-linking agents, coupling agents, branching agents and chain extenders include polymers prepared with these agents wherein the agent has undergone further reaction during processing. For example, the agent may undergo dehydration during polymerization. Thus, poly (butylene succinate)-malic acid copolymer refers to a copolymer prepared from succinic acid, 1,4-butanediol and malic acid. In some embodiments, malic acid may be used as a branching or cross-linking agent to prepare a copolymer of poly(butylene succinate) with adipate, which may be referred to as poly[(butylene succinate)-co-adipate] cross-linked with malic acid. As used herein, "poly(butylene succinate) and copolymers" includes polymers and copolymers prepared with one or more of the following: chain extenders, coupling agents, cross-linking agents and branching agents. In some embodiments, the poly(butylene succinate) and copolymers thereof contain at least 70%, 80%, and/or 90% by weight of succinic acid and 1,4-butanediol units. The polymers comprising diacid and diols, including poly(butylene succinate) and copolymers thereof and others described herein, may have a weight average molecular weight (Mw) of 10,000 to 400,000, 50,000 to 300,000, and/or 100,000 to 200,000 based on gel permeation chromatography (GPC) relative to polystyrene standards. In some embodiments, the polymers and copolymers have a weight average molecular weight of 50,000 to 300,000, and/or 75,000 to 300,000. In some embodiments, the poly (butylene succinate) or copolymer thereof used to make the scaffold has one or more, or all of the following properties: density of 1.23-1.26 g/cm$^3$, glass transition temperature of −31° C. to −35° C., melting point of 113° C. to 117° C., melt flow rate (MFR) at 190° C./2.16 kgf of 2 to 10 g/10 min, and tensile strength of 30 to 60 MPa.

In another embodiment, the polymers and copolymers described herein that are used to prepare the scaffold of the implant, including P4HB and copolymers thereof and PBS and copolymers thereof, include polymers and copolymers in which known isotopes of hydrogen, carbon and/or oxygen are enriched. Hydrogen has three naturally occurring isotopes, which include $^1$H (protium), $^2$H (deuterium) and $^3$H (tritium), the most common of which is the $^1$H isotope. The isotopic content of the polymer or copolymer can be enriched for example, so that the polymer or copolymer contains a higher than natural ratio of a specific isotope or isotopes. The carbon and oxygen content of the polymer or copolymer can also be enriched to contain higher than natural ratios of isotopes of carbon and oxygen, including, but not limited to $^{13}$C, $^{14}$C, $^{17}$O or $^{18}$O. Other isotopes of carbon, hydrogen and oxygen are known to one of ordinary skill in the art. An exemplary non-limiting hydrogen isotope enriched in P4HB or copolymer thereof or PBS or copolymer thereof is deuterium, i.e. deuterated P4HB or copolymer thereof or deuterated PBS or copolymer thereof. The percent deuteration can be up to at least 1% and up to 5, 10, 15, 20, 25, 30, 35, 40, 45, 50, 55, 60, 65, 70, 75, 80 or 85% or greater.

In some embodiments, the polymers and copolymers that are used to prepare the scaffold, including P4HB and copolymers thereof and PBS and copolymers thereof, have low moisture contents. This may ensure the implants can be produced with high tensile strength, prolonged strength retention, and good shelf life. In some embodiments, the polymers and copolymers that are used to prepare the implants have a moisture content of less than 1,000 ppm (0.1 wt %), less than 500 ppm (0.05 wt %), less than 300 ppm (0.03 wt %), less than 100 ppm (0.01 wt %), and/or less than 50 ppm (0.005 wt %).

The compositions used to prepare the implants desirably have a low endotoxin content. In some embodiments, the endotoxin content may be low enough so that the implants produced from the polymer compositions have an endotoxin content of less than 20 endotoxin units per device as determined by the limulus amebocyte lysate (LAL) assay. In one embodiment, the polymeric compositions used to prepare the scaffold of the implant have an endotoxin content of <2.5 EU/g of polymer or copolymer. For example, the P4HB polymer or copolymer, or PBS polymer of copolymer have an endotoxin content of <2.5 EU/g of polymer or copolymer.

B. Additives

In some embodiments, certain additives may be incorporated into the implant, for example, in the polymeric compositions that are used to make the scaffold. In one embodiment, these additives are incorporated with the polymers or copolymers described herein during a compounding process to produce pellets that can be subsequently processed to produce the scaffolds. For example, pellets may be extruded or printed to form the filaments of the scaffolds. In another embodiment, the pellets may be ground to produce powders suitable for further processing, for example, by 3D printing. Or, in some embodiments, powders suitable for further processing, for example by 3D printing, may be formed directly by blending the additives and polymer or copolymer. If necessary, powders used for processing may be sieved to select an optimum particle size range. In another embodiment, the additives may be incorporated into the polymeric compositions used to prepare the scaffolds of the implants using a solution-based process.

In some embodiments, the additives may be biocompatible, and/or the additives are both biocompatible and absorbable.

In one embodiment, the additives may be nucleating agents and/or plasticizers. These additives may be added to the polymeric compositions used to prepare the scaffolds of the implants in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to facilitate fabrication of the scaffold, and to improve the mechanical properties of the scaffold. Exemplary non-limiting nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the polymeric compositions for preparing the scaffolds of the implants include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl)dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. In some embodiments, the plasticizers may be citrate esters.

C. Bioactive Agents, Cells and Tissues

The implants can be loaded, filled, coated, or otherwise incorporated with bioactive agents. Bioactive agents may be included in the implants for a variety of reasons. For example, bioactive agents may be included in order to improve tissue in-growth into the implant, to improve tissue maturation, to provide for the delivery of an active agent, to improve wettability of the implant, to prevent infection, and to improve cell attachment. The bioactive agents may also be incorporated into the scaffold structure of the implant.

The implants can contain active agents designed to stimulate cell in-growth, including growth factors, cell adhesion factors including cell adhesion polypeptides, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The implants can incorporate wetting agents designed to improve the wettability of the surfaces of the scaffold structures to allow fluids to be easily adsorbed onto the implant surfaces, and to promote cell attachment and/or modify the water contact angle of the implant surface. Examples of wetting agents include polymers of ethylene oxide and propylene oxide, such as polyethylene oxide, polypropylene oxide, or copolymers of these, such as PLURONICS®. Other suitable wetting agents include surfactants, emulsifiers, and proteins such as gelatin.

The implants can contain gels, hydrogels or living hydrogel hybrids to further improve wetting properties and to promote cellular growth throughout the scaffold structures of the implants. Hydrogel hybrids consist of living cells encapsulated in a biocompatible hydrogel, for example, gelatin, methacrylated gelatin (GelMa), silk gels, and hyaluronic acid (HA) gels.

Other bioactive agents that can be incorporated in the implants include antimicrobial agents, in particular antibiotics, disinfectants, oncological agents, anti-scarring agents, anti-inflammatory agents, anesthetics, small molecule drugs, anti-adhesion agents, inhibitors of cell proliferation, anti-angiogenic factors and pro-angiogenic factors, immunomodulatory agents, and blood clotting agents. The bioactive agents may be proteins such as collagen (including recombinant collagen) and antibodies, peptides, polysaccharides such as chitosan, alginate, hyaluronic acid and derivatives thereof, nucleic acid molecules, small molecular weight compounds such as steroids, inorganic materials such as hydroxyapatite and ceramics, or complex mixtures such as platelet rich plasma. Suitable antimicrobial agents include: bacitracin, biguanide, triclosan, gentamicin, minocycline, rifampin, vancomycin, cephalosporins, copper, zinc, silver, and gold. Nucleic acid molecules may include DNA, RNA, siRNA, miRNA, antisense or aptamers.

The implants may also contain allograft material and xenograft materials, including acellular dermal matrix material and small intestinal submucosa (SIS).

In embodiments, the implants may contain a vascular pedicle, vascular pedicle perforator, or other tissue mass. The vascular pedicle, vascular pedicle perforator, or other tissue mass may be autologous tissues, allograft tissues, or xenograft tissues.

In another embodiment, the implants may incorporate systems for the controlled release of the therapeutic or prophylactic agents.

In an embodiment, the implants are coated with autograft, allograft or xenograft tissue and cells prior to implantation, during implantation, or after implantation, or any combination thereof. In some embodiments, the implants are coated with autologous tissue and cells from the patient prior to implantation, during implantation, or after implantation, or any combination thereof. The autologous tissue and cells may be one or more of the following: autologous fat, fat lipoaspirate, fat tissue, injectable fat, adipose tissue, adipose cells, fibroblast cells, and stem cells, including human adipose tissue-derived stem cells, also known as preadipocytes or adipose tissue-derived precursor cells, and fibroblast-like stem cells. In some embodiments, the implants may be coated with autologous tissue and cells as described herein, and may also further comprise a vascular pedicle, vascular pedicle perforator, or other tissue mass. As will be evident herein, the scaffold structures of the implants are designed to create not only the shape of a breast implant, but also a large surface area that can retain the autologous tissue and cells to encourage tissue in-growth.

III. Methods for Preparing Implants With at Least Two Adjacent Parallel Planes of Filaments Bonded to Each Other A variety of methods can be used to manufacture the implants.

In embodiments, the implant is prepared so that it is able to provide one or more of the following: (i) structural support, (ii) a scaffold for tissue ingrowth, (iii) a scaffold for delivering cells, tissues, collagen, recombinant collagen, hyaluronic acid, and bioactive agents, including fat, lipoaspirate, adipose cells, fibroblast cells, and stem cells (iv) a structure that can provide mechanical spacing, (v) a structure that can allow incorporation of a graft into the scaffold structure, such as a vascular pedicle or other tissue mass, (vi) a structure that can be coated with cells, tissues, collagen, recombinant collagen, hyaluronic acid, and bioactive agents, including fat, lipoaspirate, adipose cells, fibroblast cells, and stem cells on the inside of the scaffold by injection using a needle, (vii) a structure with properties similar (meaning within ±50% of a property value) or the same as soft tissues of the breast, (viii) a structure with an compressive modulus that is within ±50%, and/or within ±25% of the compressive modulus value of breast tissue, (viii) a structure with a high strength relative to its volumetric density, (ix) a structure with a compressive design and/or a spring design (meaning that the scaffold may be deformed by a force and recover its original shape when the force is removed), and (x) a structure with anisotropic mechanical properties.

A. Implant Shapes

In an embodiment, the implants are designed so that when manufactured, they are three-dimensional. In embodiments, the implants are designed to be used instead of permanent breast implants, such as silicone and saline breast implants.

The implant's shape allows the surgeon to increase tissue volume, reconstruct lost or missing tissue or tissue structures, contour tissues, augment tissues, restore tissue function, repair damaged tissue structures, enhance an existing tissue structure, increase soft tissue volume, alter the projection of the breast, increase upper pole fullness, and reshape the breast. In some embodiments, the implants are used to reshape or repair the breast, augment the breast, and to repair the breast following mastectomy. In an embodiment, the implants allow the shape of soft tissue structures to be altered, or sculpted, without the use of permanent implants.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Figure 1D:
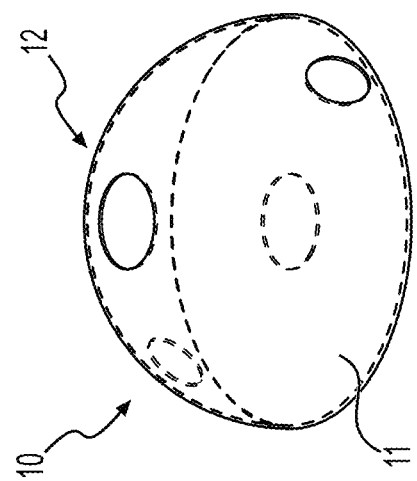
FIG. 1D is a side view of a breast implant scaffold 30 shown in FIG. 1A with a front area 31 and a back area 32.
Figure 1A:
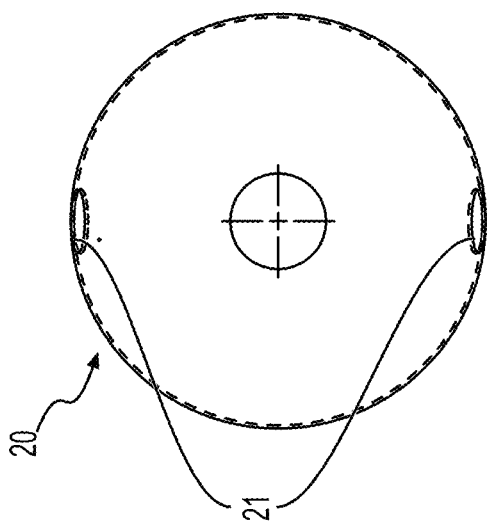
FIG. 1A is an isometric view of a breast implant scaffold 1 in accordance with one embodiment of the invention. The breast implant scaffold 1 is shown with a back area 2 for placement on the chest wall of the patient, a front area 3 opposite the back area, a front bottom 4 for placement in the lower pole of the breast, a front top 5 for placement in the upper pole of the breast, a front intermediate-region 6 for placement under the skin of the patient, an opening 7 between the back area and front area for insertion of a tissue mass, and an opening 8 perpendicular to opening 7 for insertion of a second tissue mass.
Figure 1B:
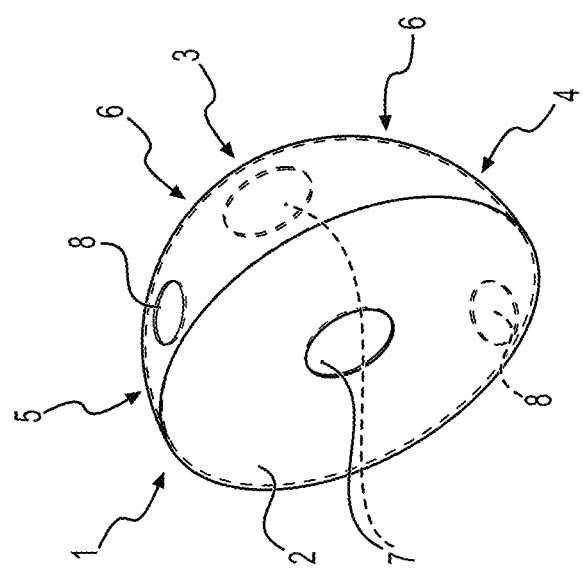
FIG. 1B is a second isometric view of a breast implant scaffold 10 shown in FIG. 1A with a back area 11 and a front area 12.

In embodiments, and with reference to FIG. 1A, a breast implant scaffold 1 comprises a back area 2 for placement on the chest wall of the patient, a front area 3 opposite the back area, the front area comprising a front bottom 4 for placement in the lower pole of the breast, a front top 5 for placement in the upper pole of the breast, and a front intermediate-region 6 for placement under the skin of the patient as shown in FIG. 1A. FIG. 1B shows a second isometric view of a breast implant scaffold 10 with a back area 11 and a front area 12. FIG. 1D is a side view of a breast implant scaffold 30 with a front area 31 and a back area 32.

The front area of the breast implant is shaped to provide projection to the breast. The projection of the implant as used herein is the maximum distance between the back area and the front area of the implant.

In embodiments, the front bottom area of the implant comprises a convex exterior surface. The convex exterior surface shape of the implant provides a pleasing anatomical shape to the lower pole of the breast.

Within the scope described herein, it should be understood that there are a plurality of implant shapes and dimensions, and that the invention is not limited with regard to the three-dimensional shape and dimensions of the implant, except where recited in the appended claims. The implants can be assembled or printed to have any size and shape suitable for use as an implant. For example, implants can easily be prepared that have three-dimensional shapes such as a: sphere, hemisphere, cylinder, cone, dome, cuboid, tetrahedron, triangular or square prism, dodecahedron, torus, and ellipsoid, and custom shapes can be produced optionally with the assistance of computer-aided design. For example, one can produce a dome shaped implant for the reconstruction of a breast.

The implants may have different shapes in the front bottom and front top areas of the implant. The dimensions of the implant may be sized to augment breast tissue volume, to substitute for prior breast tissue volume, to change the volumetric distributions of breast tissue, to change the appearance of breast tissues, or to replace existing breast tissue volume with a smaller volume. The implants may be sized or shaped to provide a low, moderate, or high profile shape to the breast, wherein the implant profile determines the projection of the breast. High profile shaped implants may be used to increase the height of the breast side wall, and provide patients with more upper pole fullness, or cleavage. Smaller increases in the height of the breast side wall may be obtained using implants with low or moderate profile shapes. The implants may be designed for use in the breast in sizes large enough to allow for their use in mastopexy and breast reconstruction. In embodiments, the breast implants have a volume between 100 and 1200 cc (cubic centimeters), and/or a volume between 120 and 850 cc. In embodiments, the implants are wide enough to span the width of a breast. In embodiments, the width of the back area of the implants is between 6 and 20 cm, and/or between 8 and 18 cm. The projection of the implant as used herein is the maximum distance between the back area and the front area of the implant. In embodiments, the projection of the implant is between 2 and 15 cm, between 3 and 10 cm, and/or between 4 and 7 cm.

In some embodiments, implants are provided in shapes that can be used to alter the soft tissue volume of a breast without the use of a permanent breast implant, such as a silicone breast implant. In embodiments, the implants can be prepared in shapes and sizes for use in augmenting the size of a breast, replacing the tissue volume and shape of the breast following a mastectomy procedure, to remove a defect in the breast, and to produce a specific appearance of the breast. For example, the implant can be prepared so that when implanted in the breast it produces a breast with a specific ratio of upper pole volume (UPV) to lower pole volume (LPV). In embodiments, the implant is a breast implant that has volumetric dimensions such that implantation of the implant results in a breast with an UPV of 25-35% of total breast volume, and LPV of 65-75% of total breast volume. In addition to sculpting the breast with specific volumetric ratios of tissue in the upper and lower poles, the dimensions and shape of the implant can also be chosen to provide very desirable shapes of the lower pole, upper pole, and extent of projection of the breast from the chest wall. In embodiments, the implants are designed so that (a) the lower pole of the breast has a very attractive lower pole curvature, specifically an attractive convex shape, (b) the upper pole of the breast has a straight or slightly concave curvature, and (c) the distance the breast projects from the breast wall is defined. It will therefore be apparent that the implants of the invention can be used to produce a very attractive reconstructed breast by having specific shapes that (i) define the ratio of the UPV to the LPV; (ii) define the curvatures of the upper and lower poles; (iii) define the extent of projection of the breast from the chest wall; and (iv) define the angulation of the nipple on the breast.

The shape of the implants may vary. Non-limiting examples of shapes include: round, teardrop, anatomically-breast shaped, or anatomically-breast contoured.

Additional shapes for the implant are set forth in U.S. patent application Ser. No. 16/262,018, filed Jan. 30, 2019 and entitled "FULL CONTOUR BREAST IMPLANT", and incorporated herein by reference in its entirety.

In embodiments, the implants comprise one or more openings for insertion of one or more tissue masses. In some embodiments, the implants comprise one or more openings on the back area of the implant. One or more openings in the back area of the implant allow the surgeon to insert one or more pedicles into the implant when the back area of the implant is implanted on the chest wall. The one or more openings in the implant may create a chamber in the implant, or may create a passage through the implant. For example, an opening 7 may extend from the back area of the implant to the front area of the implant as shown in FIG. 1A. In embodiments, the implants may comprise an opening 21 extending in a medial to lateral direction as shown in FIG. 1C for insertion of a tissue mass. In embodiments, the implants may comprise one or more openings in the front area of the implant, the front bottom, the front top or the front intermediate-region. The dimensions of the one or more openings are sized to receive the tissue mass.

B. Construction of the Implants

The implants comprise a scaffold, and the scaffold comprises filaments.

In embodiments, the filaments of the scaffold are applied or printed in separate or individual layers (e.g., one layer at a time on top of each other, namely, stacked). A second layer of filaments having filaments oriented in a second direction, or angle, are applied on top of a first layer of filaments, wherein the first layer of filaments is oriented in a first direction or angle. Additional layers of filaments may be added to build up a porous structure comprising layers of filaments. Applying layers of filaments in this manner, having different orientations, creates a crisscross, triangular, square, quadrilateral, parallelogram, or other polygon-like open pore structure when viewed from the top or bottom of the scaffold of the implant as shown, for example, in FIGS. 2-6.

The number of layers having different orientation or printer angles (when the implant is 3D printed) may vary. In embodiments, 2-3 different types of layer orientations are applied. However, in other embodiments, 3-5, or more different types or print angles or layer orientations are provided.

Figure 2A:
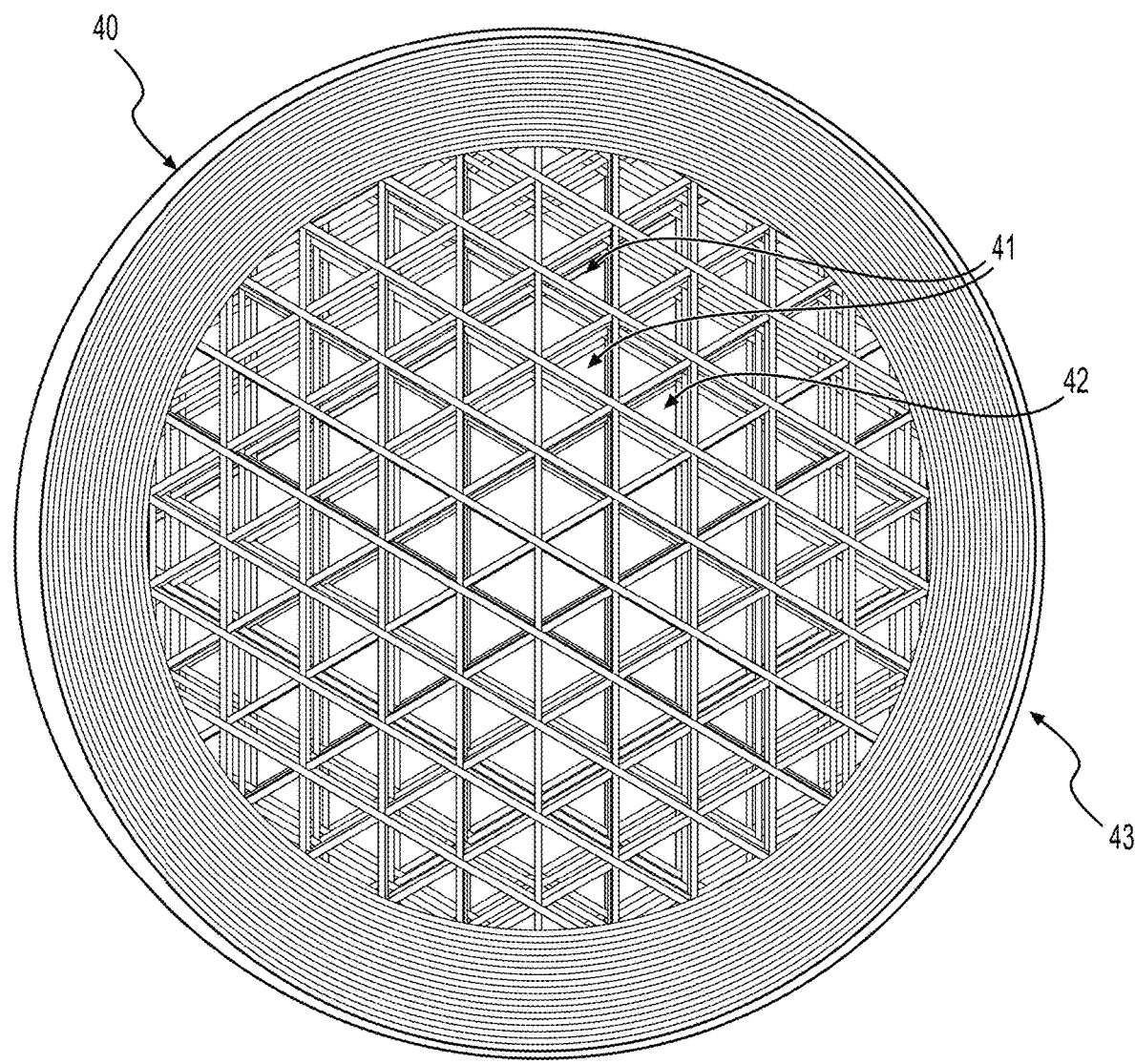
FIG. 2A is a top view of a cross section along the mid plane of a breast implant 40 in accordance with one embodiment of the invention. The breast implant scaffold 40 is shown having stacking layers of parallel filaments with each subsequent layer of filaments crisscrossed with the prior layer of filaments, at a 60-degree angle, to form a porous infill pattern. Every fourth layer of filaments is oriented in the same direction. The implant has an outer shell prepared from concentric stacks of a single filament at the periphery of the implant that enclose the stacked layers of parallel filaments.
Figure 2B:
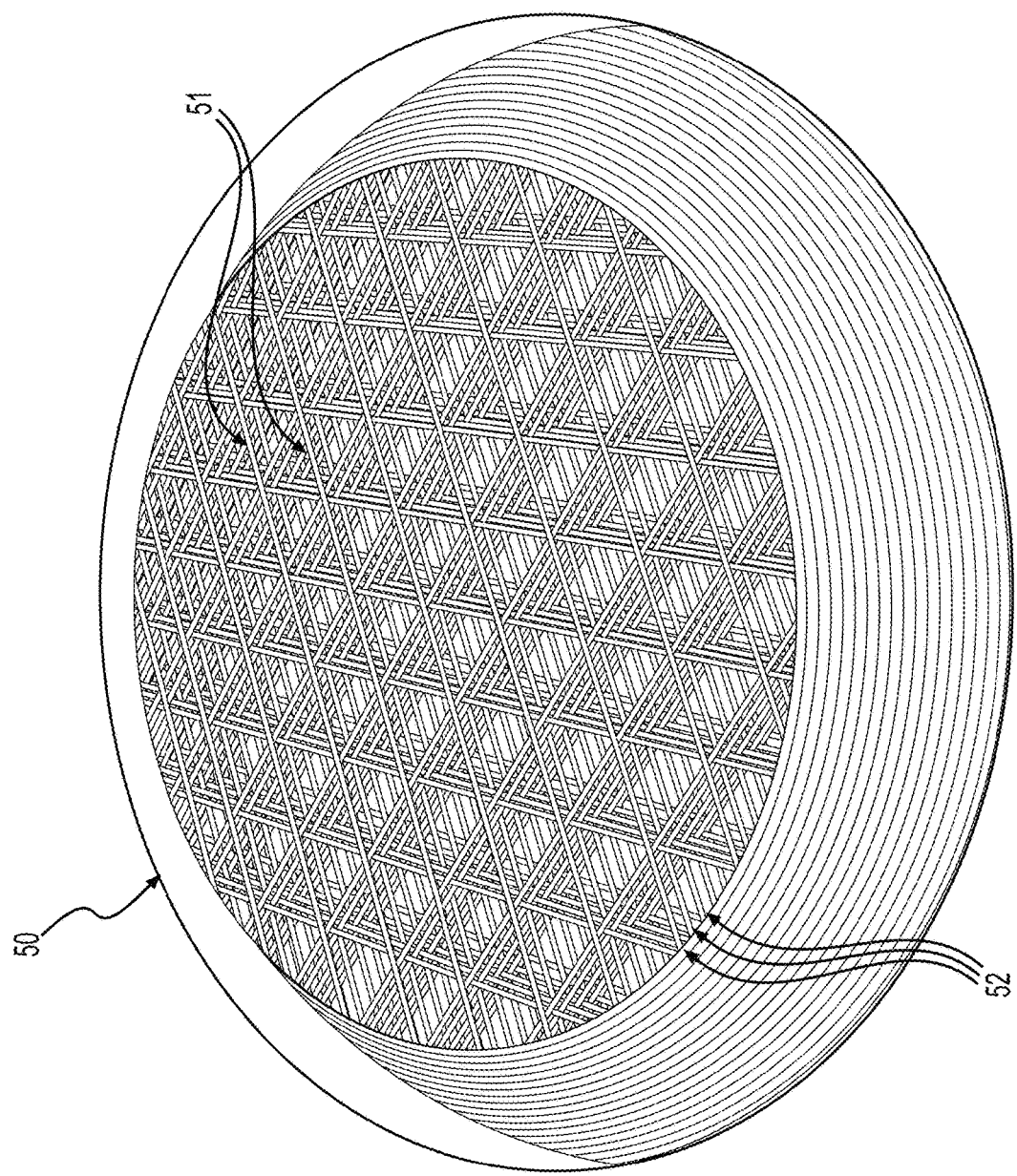
FIG. 2B is a partial isometric view of the cross section along the mid plane of a breast implant 50 shown in FIG. 2A, prepared by stacking layers of parallel filaments with each subsequent layer of filaments crisscrossed with the prior layer of filaments, at a 60-degree angle, to form a porous infill pattern. Every fourth layer of filaments is oriented in the same direction. The implant has an outer shell prepared from concentric stacks of a single filament at the periphery of the implant that enclose the stacked layers of parallel filaments.

Within a single layer of filaments, each filament can have the same orientation or direction. For example, as shown in FIGS. 2A and 2B, the filaments in each layer extend in the same direction and are generally parallel to one another.

In embodiments, the angles between successive layers of parallel filaments may range from 0 to 179 degrees, 0 to 90 degrees, and/or 0 to 60 degrees. Implants with different compressive modulus values may be constructed by varying the angles between successive layers of parallel filaments. For example, the angles may be varied to form implants with compressive modulus values ranging from 10 kPa to 100 MPa, and/or 20 kPa to 1 MPa. In embodiments, the angles are selected to provide implants that can be compressed, and recover from compression. In embodiments, the angles are selected so that the implant in the breast does not feel hard.

In embodiments, the implant comprises layers of parallel filaments with at least one layer of parallel filaments angled at 1-60 degrees from another layer of parallel filaments. In embodiments, the implant comprises layers of filaments where the parallel filaments of a first layer are angled at an angle ($\alpha$) from an adjacent layer of filaments, where a is a multiple of 2, 3 or 5 between 0 and 60 degrees. In embodiments, angle $\alpha$ is 18, 20, 24, 30, 36, 45 or 60 degrees, from another adjacent layer of parallel filaments.

In embodiments, the distances between the filaments in a layer are equal. However, in other embodiments (not shown), the distances between filaments within a single layer are not equal, and may vary within the layer, or vary from layer to layer.

In embodiments, the scaffold of the implant comprises at least two layers of filaments bonded to each other. In other embodiments, all layers of filaments in the scaffold are bonded to at least one other layer of filaments.

In embodiments, implant scaffolds with at least two adjacent parallel planes of filaments bonded to each other may be prepared with the filaments in adjacent or nonadjacent planes having the same orientation as each other, or different orientations to each other. Forming scaffolds comprising filaments in adjacent layers with the same orientations to each other may be used to increase the porosity of the implant or to alter the compression modulus of the implant.

In embodiments, the three-dimensional architecture of the implant may comprise two or more adjacent layers of parallel filaments where there is no offset or angle between the layers of parallel filaments. In these embodiments, filaments in an adjacent layer are placed on top of each other so that there is no angle between them, and so that they do not form a crisscross structure. Incorporating sections of adjacent layers where the filaments in each layer have the same orientation may be used to produce implants with larger pore sizes. For example, an implant may be formed where successive layers of parallel filaments are first angled from the prior layers by 60 degrees, followed by a section where adjacent layers are not angled, followed by successive layers again angled at 60 degrees to the prior layer.

Figure 7:
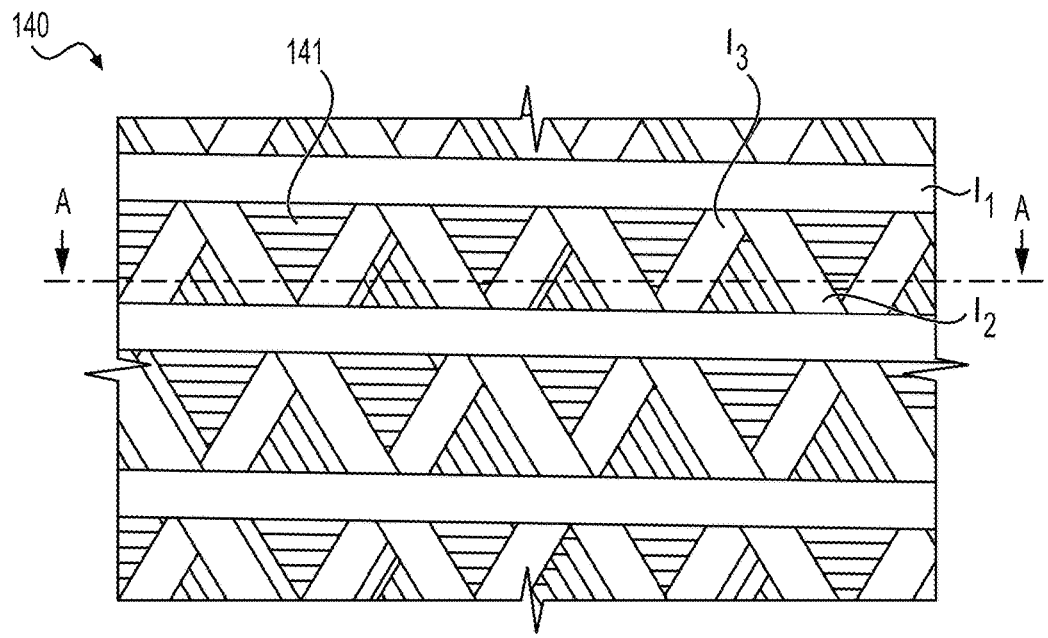
FIG. 7 is an enlarged portion of a breast implant scaffold 140 viewed from the top in accordance with an embodiment of the invention showing a triangular open pore structure 141 with layers of crisscrossed filaments $I_1$, $I_2$ and $I_3$.

The architecture used to prepare the implant's scaffold may be selected based on the desired properties of the scaffold. For example, the filaments in each layer may be printed at 0, 60, and 120-degree angles to each other forming a triangular open pore structure as shown in FIGS. 2A and 2B. An enlarged portion of an exemplary triangular-shaped pore structure 140 is illustrated in FIG. 7. The triangular open pore structure 141 is generally defined by stacking layers of filaments such that the filaments (e.g., $I_1$, $I_2$, $I_3$) crisscross. In FIG. 7, there are three types of layers including a first layer having filaments arranged at 0 degrees from horizontal corresponding to filament(s) $I_1$; a second type of layer having filaments orientated at 60 degrees from horizontal corresponding to filament $I_3$, and a third type of layer having filaments arranged at 120 degrees from horizontal corresponding to filament $I_2$. Collectively, the arrangement of the layers having filaments oriented at different angles creates the triangular open pore structure 141 shown in FIG. 7 serving to facilitate tissue ingrowth into the breast implant scaffold.

Figure 8:
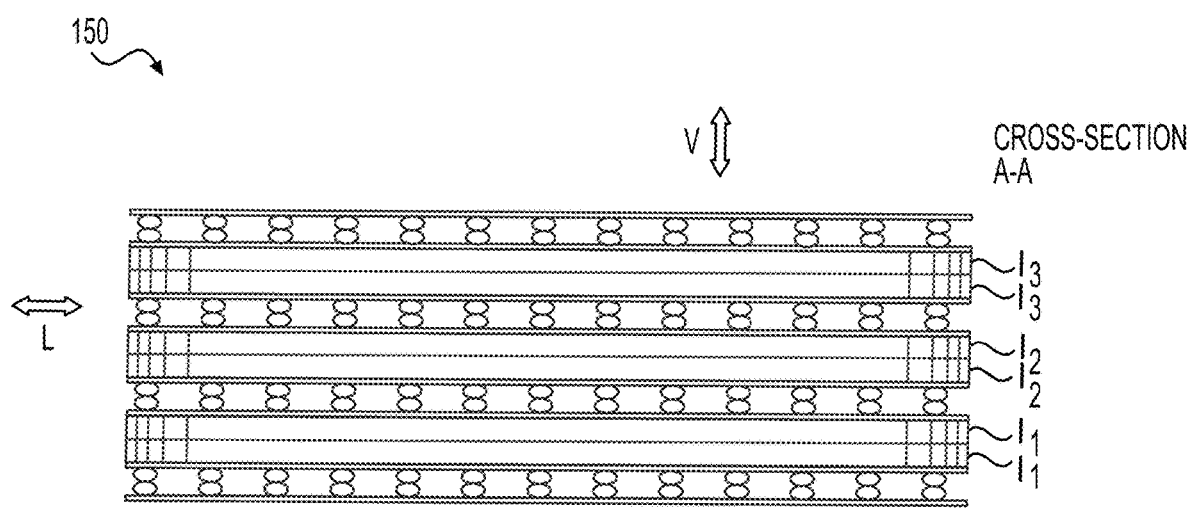
FIG. 8 is a cross sectional view of a breast implant scaffold 150 shown in FIG. 7, taken along line A-A in accordance with an embodiment of the invention, prepared by repeating each filament layer of the scaffold before changing the print angle or filament orientation of the filament layer, serving to increase lateral porosity (L) relative to the vertical porosity (V).

FIG. 8 shows a cross sectional view of the breast implant scaffold 150 shown in FIG. 7, taken along line A-A, with an open pore structure (like that shown in FIG. 2A) but where the lateral porosity (L) has been enlarged by once repeating the printing of each filament layer (e.g., $I_1$, $I_1$) before changing the filament orientation or print angle (when the implant is 3D printed). Repeating a layer of filaments with the same orientation creates an "effective layer" that is double in height (e.g., effective first layer comprises $I_1$ and $I_1$) and increases the lateral porosity (L) of the implant's scaffold. In embodiments, the lateral porosity (L) is different than the vertical porosity (V). The lateral porosity can be less than or greater than the vertical porosity (V). In embodiments, the lateral porosity is adjusted relative to the vertical porosity by increasing or decreasing the number of repeated layers of filaments with the same orientation.

Repeated printing of layers before changing the print angle may also be used to change the compressive modulus of the scaffold of the implant. In the example shown in FIG. 8, two filament layers are printed at an angle of 0 degrees, the print angle is then changed and two filament layers are printed at an angle of 60 degrees before two filament layers are printed at another angle such as e.g., an angle of 120 degrees. The process is then repeated to build up the porous structure to the desired dimensions. In order to create even larger pore sizes, multiple layers (for example, 3, 4, 5, 6, 7, 8, 9, 10 or more) may be printed at the same angle (i.e., repeated) before the print angle is changed. It is to be understood that in accordance with the invention, these angles may be varied to form different shaped open pore structures with two or more filament layers printed at the same angle before the print angle is changed.

In embodiments, the scaffolds of the implants have pores with widths or diameters of 100 µm to 1 mm, and/or 250 µm to 750 µm. In embodiments, the pore sizes of the scaffold of the implant are the same. In embodiments, the scaffold of the implant comprises a mixture of pore sizes.

In some embodiments, the scaffolds of the implants may have an architecture that provides a larger surface area and large void volume suitable to allow the scaffold to be colonized by cells and invaded by tissue, blood vessels, or combinations thereof.

In embodiments, the average diameters of the filaments are 50 to 800 µm, 100 to 600 µm, and/or 150 to 550 µm. In embodiments, the distances between the filaments of the implant are between 50 µm and 1 mm, 100 µm and 1 mm, and/or 200 µm and 1 mm. The average diameters of the filaments and the distances between the filaments may be selected according to the properties of the implant scaffold that are desired, including the compression modulus, the porosity, and the infill density, defined as the ratio of volume occupied by filament material in the implant scaffold divided by the total volume of the scaffold expressed as a percentage. In embodiments, the infill density of the implant's scaffold is from 1 to 60 and/or from 5 to 25%.

The architecture of the implant's scaffold may provide sufficient porosity to makes it possible to coat the inside of the scaffold with allograft or xenograft tissue and cells, autologous tissue and cells, including, but not limited to, autologous fat, fat lipoaspirate, lipo-filling, injectable fat, adipose cells, fibroblast cells, and stem cells. The architecture of the implant's scaffold may be designed to allow the inner surfaces of the scaffold to be coated with collagen (including recombinant collagen) and/or hyaluronic acid or derivative thereof.

In embodiments, the dimensions of the pores of the implant's scaffold are large enough to allow needles to be inserted into the pores of the scaffold in order to deliver bioactive agents, cells, fat and other compositions by injection. In embodiments, the architecture of the scaffold is designed to allow needles with gauges of 12-21 to be inserted into the scaffold. This property allows the scaffold to be loaded with cells, tissue, collagen, bioactive agents and additives, including fat, using a syringe and without significantly damaging the scaffold. In some embodiments, the scaffolds may allow insertion of needles into the scaffolds with outer diameters of 0.5 to 3 mm.

FIG. 2A shows a top view of a breast implant 40 formed by stacking layers of parallel filaments 41 together with each successive layer of parallel filaments offset or angled from the prior layer of filaments by 60 degrees. This results in an internal implant architecture comprising triangular shaped pores 42 where the layers of filaments are stacked at 0, 60 and 120 angles to the first layer of filaments. The stacked layers of parallel filaments are surrounded by a shell 43 prepared from a stack of concentric filaments at the periphery of the implant's scaffold, and enclosing the successive layers of parallel filaments. An alternative isometric view of the same implant shown in FIG. 2A is shown in FIG. 2B as breast implant 50. The isometric view clearly shows the stacked layers of parallel filaments 51 that form the scaffold structure of breast implant 50. Filaments 51 are shown in different layers, but oriented in the same direction, and are interspersed with filaments angled at 60 and 120 degrees to create a porous scaffold.

The porosity and shapes of the pores of the implant's scaffold may be tailored by changing the offset or angle between the filaments in each layer.

Figure 3A:
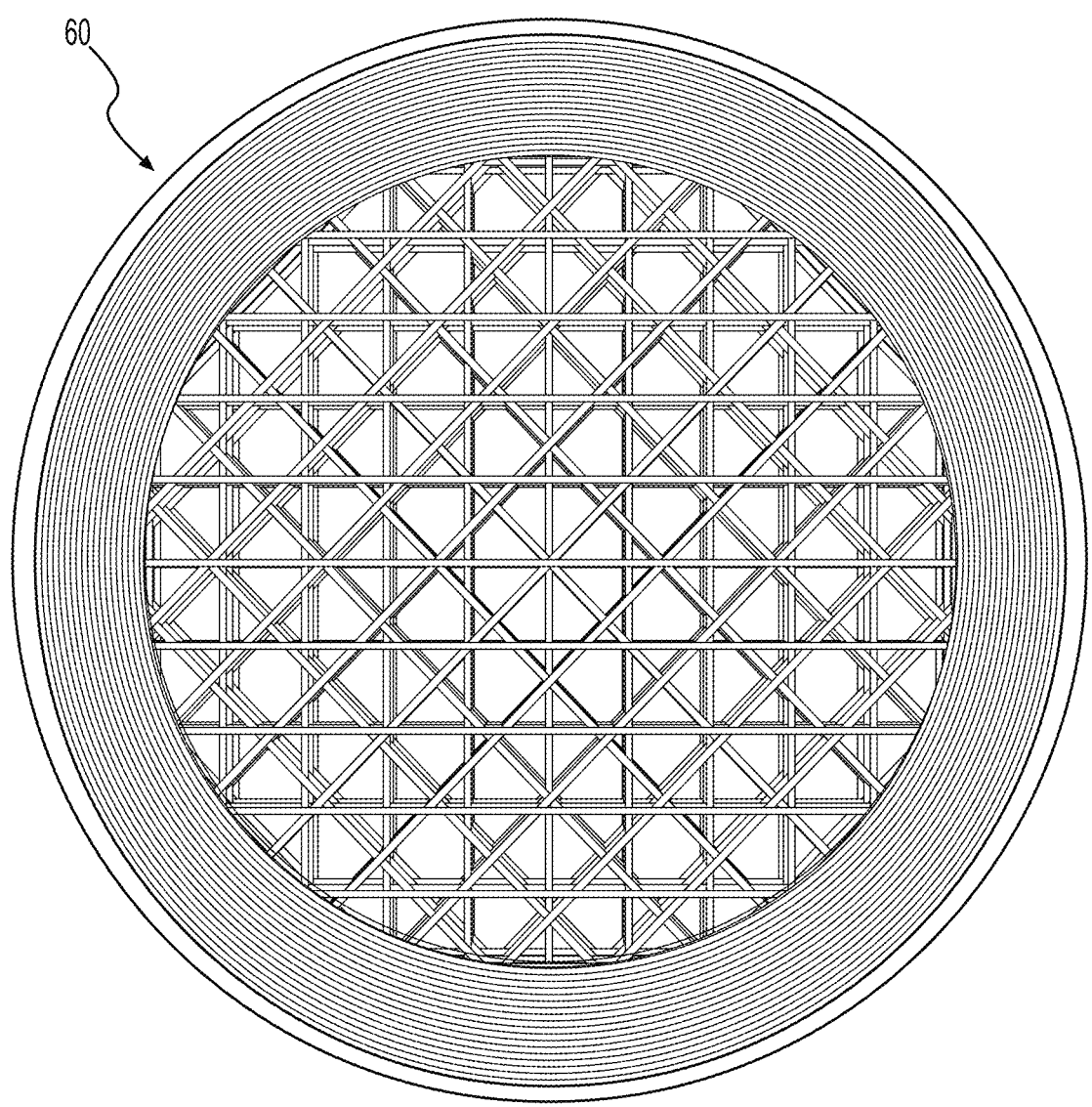
FIG. 3A is a top view of a cross section along the mid plane of a breast implant 60 in accordance with one embodiment of the invention. The breast implant scaffold 60 is shown having stacking layers of parallel filaments with each subsequent layer of filaments crisscrossed with the prior layer of filaments, at a 45-degree angle, to form a porous infill pattern. Every fifth layer of filaments is oriented in the same direction. The implant has an outer shell prepared from concentric stacks of a single filament at the periphery of the implant that enclose the stacked layers of parallel filaments.
Figure 3B:
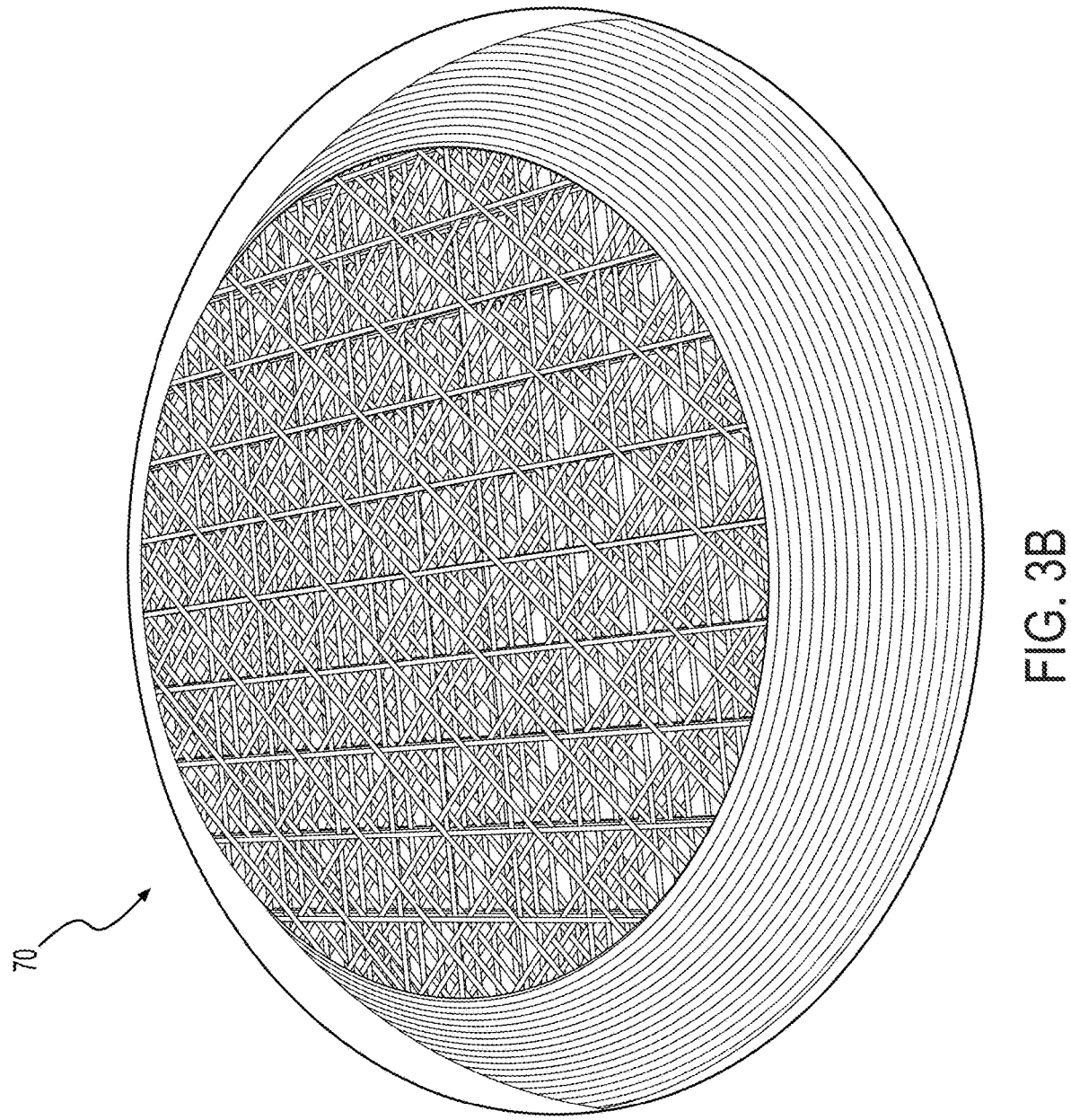
FIG. 3B is a partial isometric view of the cross section along the mid plane of a breast implant 70 shown in FIG. 3A, prepared by stacking layers of parallel filaments with each subsequent layer of filaments crisscrossed with the prior layer of filaments, at a 45-degree angle, to form a porous infill pattern. Every fifth layer of filaments is oriented in the same direction. The implant has an outer shell prepared from concentric stacks of a single filament at the periphery of the implant that enclose the stacked layers of parallel filaments.

FIG. 3A shows a top view of a breast implant 60 formed by stacking layers of parallel filaments together, with each successive layer of parallel filaments offset or angled from the prior layer of filaments by 45 degrees instead of 60 degrees. In this example, every fifth layer of filaments has the same alignment instead of every fourth layer of filaments as is the case for the implant 40 of FIG. 2A. It will be apparent by inspection of FIG. 3A that placement of the filaments in this manner changes the regular triangular pore shapes shown in FIG. 2A to a mixture of different pore shapes including pores of different sizes. An alternative isometric view of the same implant shown in FIG. 3A is shown in FIG. 3B as breast implant 70. FIG. 3B clearly shows the stacked layers of parallel filaments.

Figure 4A:
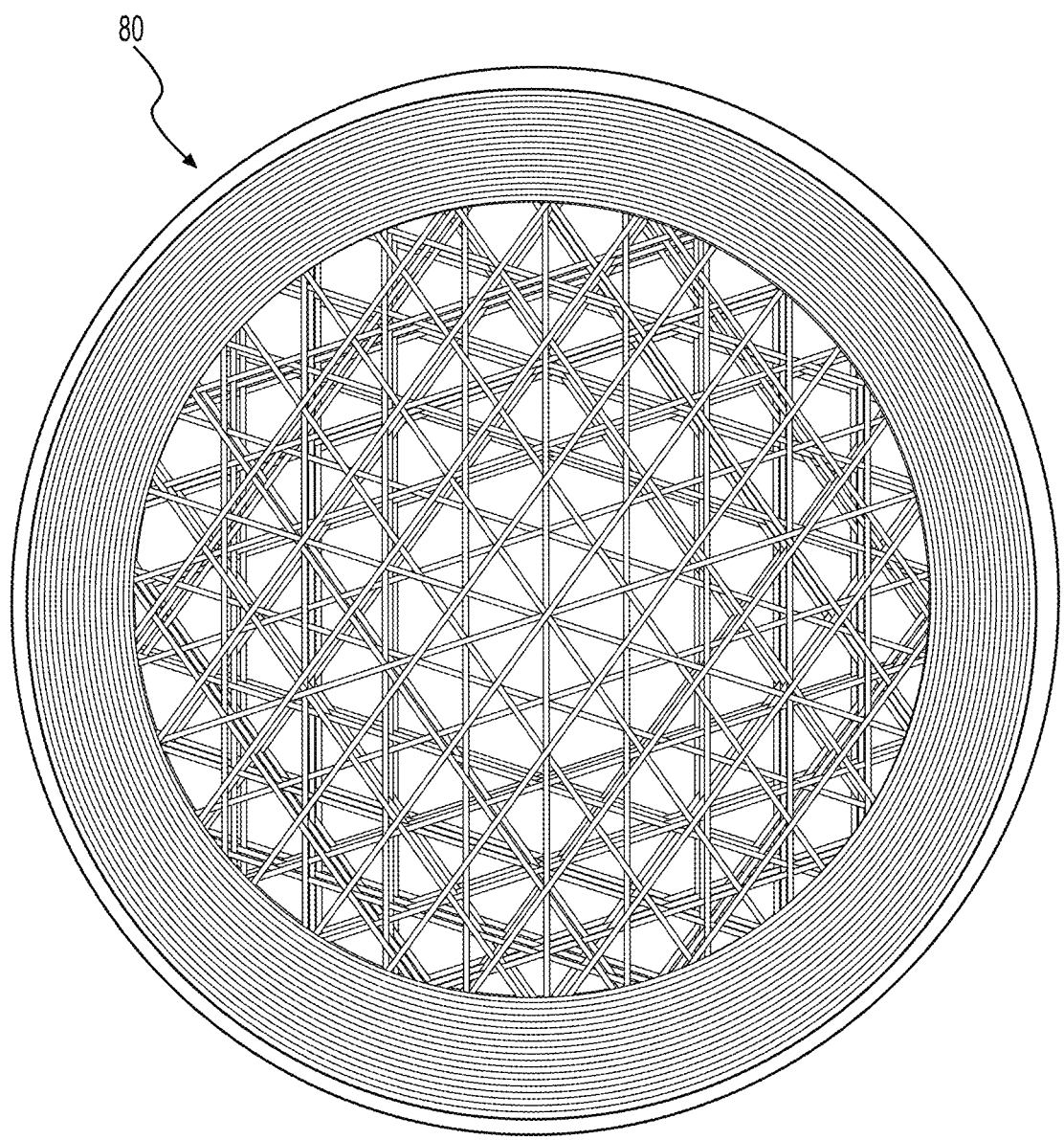
FIG. 4A is a top view of a cross section along the mid plane of the breast implant 80 in accordance with one embodiment of the invention. The breast implant scaffold 80 is shown having stacking layers of parallel filaments with each subsequent layer of filaments crisscrossed with the prior layer of filaments, at a 36-degree angle, to form a porous infill pattern. Every sixth layer of filaments is oriented in the same direction. The implant has an outer shell prepared from concentric stacks of a single filament at the periphery of the implant that enclose the stacked layers of parallel filaments.
Figure 4B:
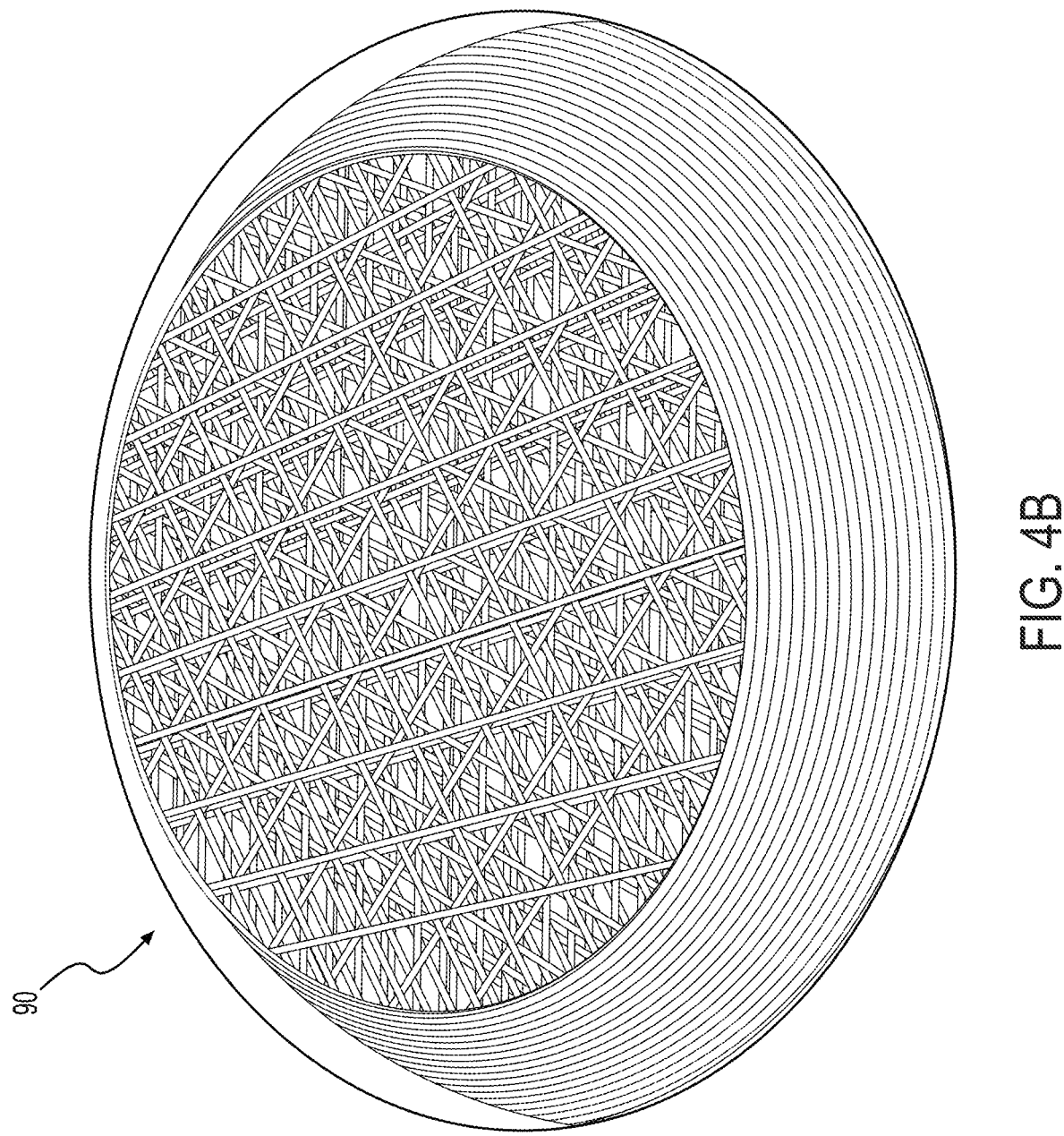
FIG. 4B is a partial isometric view of the cross section along the mid plane of the breast implant 90 shown in FIG. 4A, prepared by stacking layers of parallel filaments with each subsequent layer of filaments crisscrossed with the prior layer of filaments, at a 36-degree angle, to form a porous infill pattern. Every sixth layer of filaments is oriented in the same direction. The implant has an outer shell prepared from concentric stacks of a single filament at the periphery of the implant that enclose the stacked layers of parallel filaments.

FIG. 4A shows a top view of a breast implant 80 formed by stacking layers of parallel filaments together with each successive layer of parallel filaments offset or angled from the prior layer of filaments by 36 degrees. In this example, every sixth layer of filaments has the same alignment, and the pattern of layers produces a mixture of smaller and larger pore sizes of various shapes. An alternative isometric view of the same implant shown in FIG. 4A is shown in FIG. 4B as breast implant 90. FIG. 4B clearly shows the stacked layers of parallel filaments.

Figure 5A:
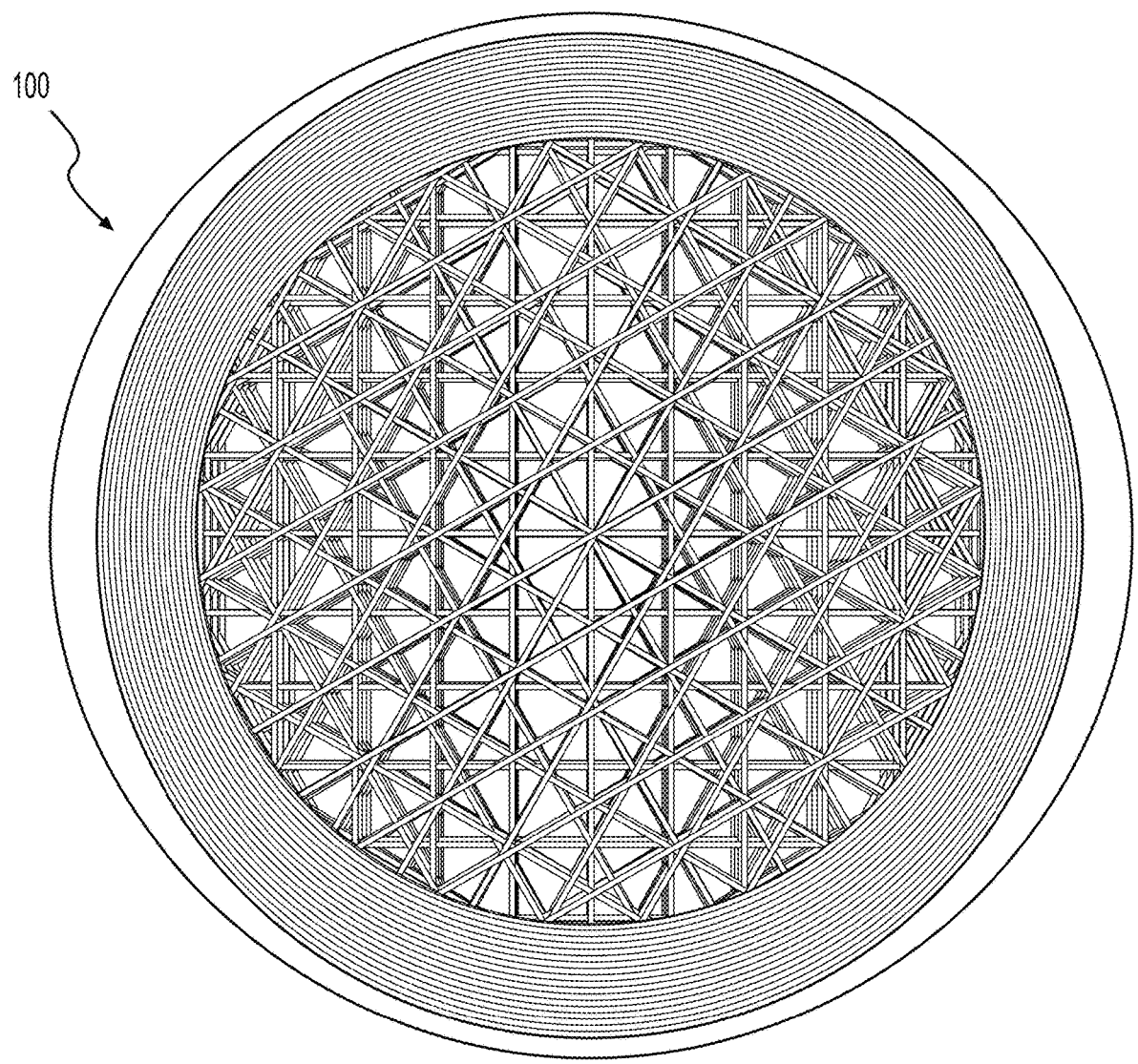
FIG. 5A is a top view of a cross section along the mid plane of a breast implant 100 in accordance with one embodiment of the invention. The breast implant scaffold 100 is shown having stacking layers of parallel filaments with each subsequent layer of filaments crisscrossed with the prior layer of filaments, at a 30-degree angle, to form a porous infill pattern. Every seventh layer of filaments is oriented in the same direction. The implant has an outer shell prepared from concentric stacks of a single filament at the periphery of the implant that enclose the stacked layers of parallel filaments.
Figure 5B:
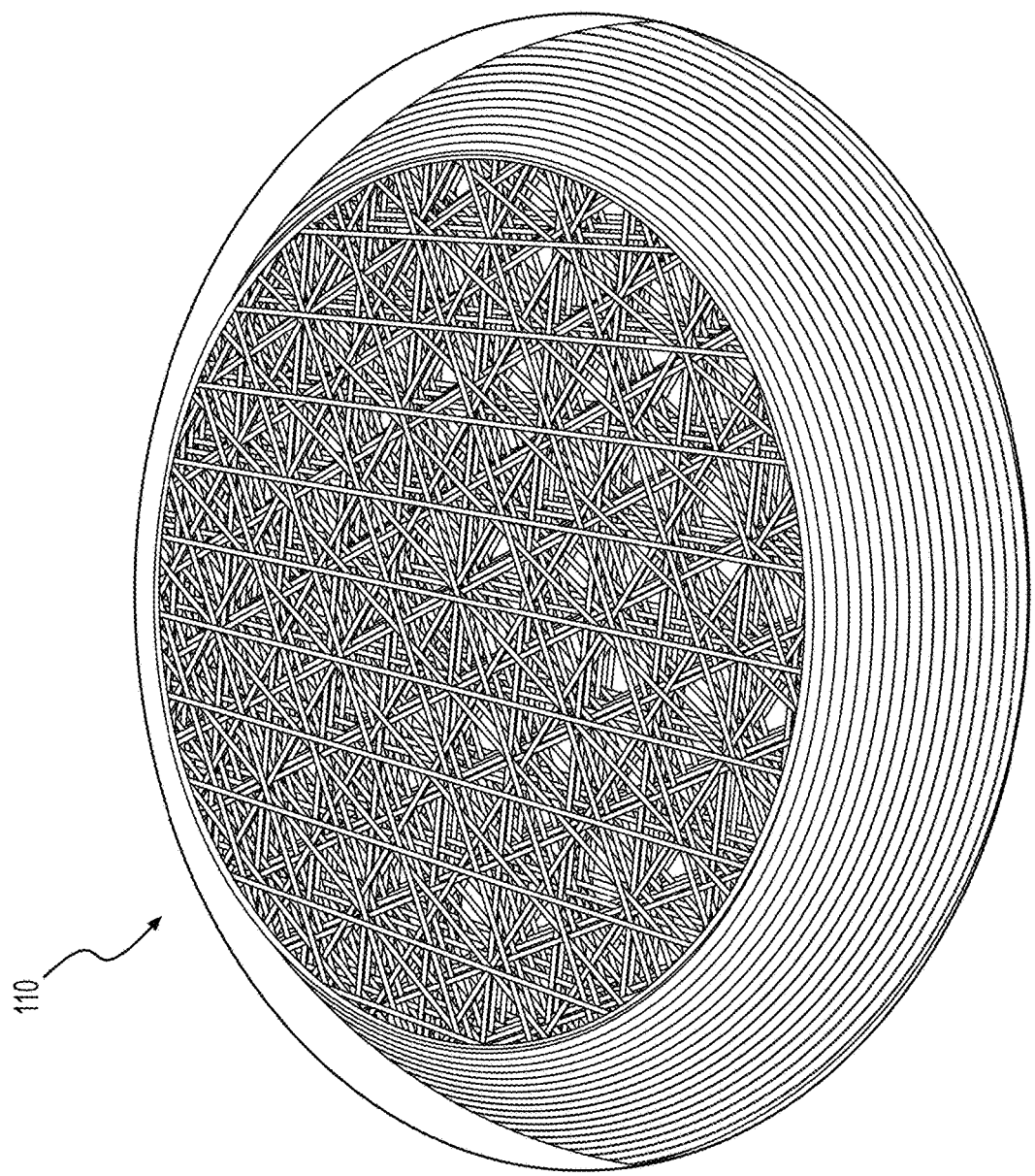
FIG. 5B is a partial isometric view of the cross section along the mid plane of a breast implant 110 shown in FIG. 5A, prepared by stacking layers of parallel filaments with each subsequent layer of filaments crisscrossed with the prior layer of filaments, at a 30-degree angle, to form a porous infill pattern. Every seventh layer of filaments is oriented in the same direction. The implant has an outer shell prepared from concentric stacks of a single filament at the periphery of the implant that enclose the stacked layers of parallel filaments.

FIG. 5A shows a top view of a breast implant 100 formed by stacking layers of parallel filaments together with each successive layer of parallel filaments offset or angled from the prior layer of filaments by 30 degrees. In this example, every seventh layer of filaments has the same alignment. An alternative isometric view of the same implant shown in FIG. 5A is shown in FIG. 5B as breast implant 110. FIG. 5B clearly shows the stacked layers of parallel filaments.

Figure 6A:
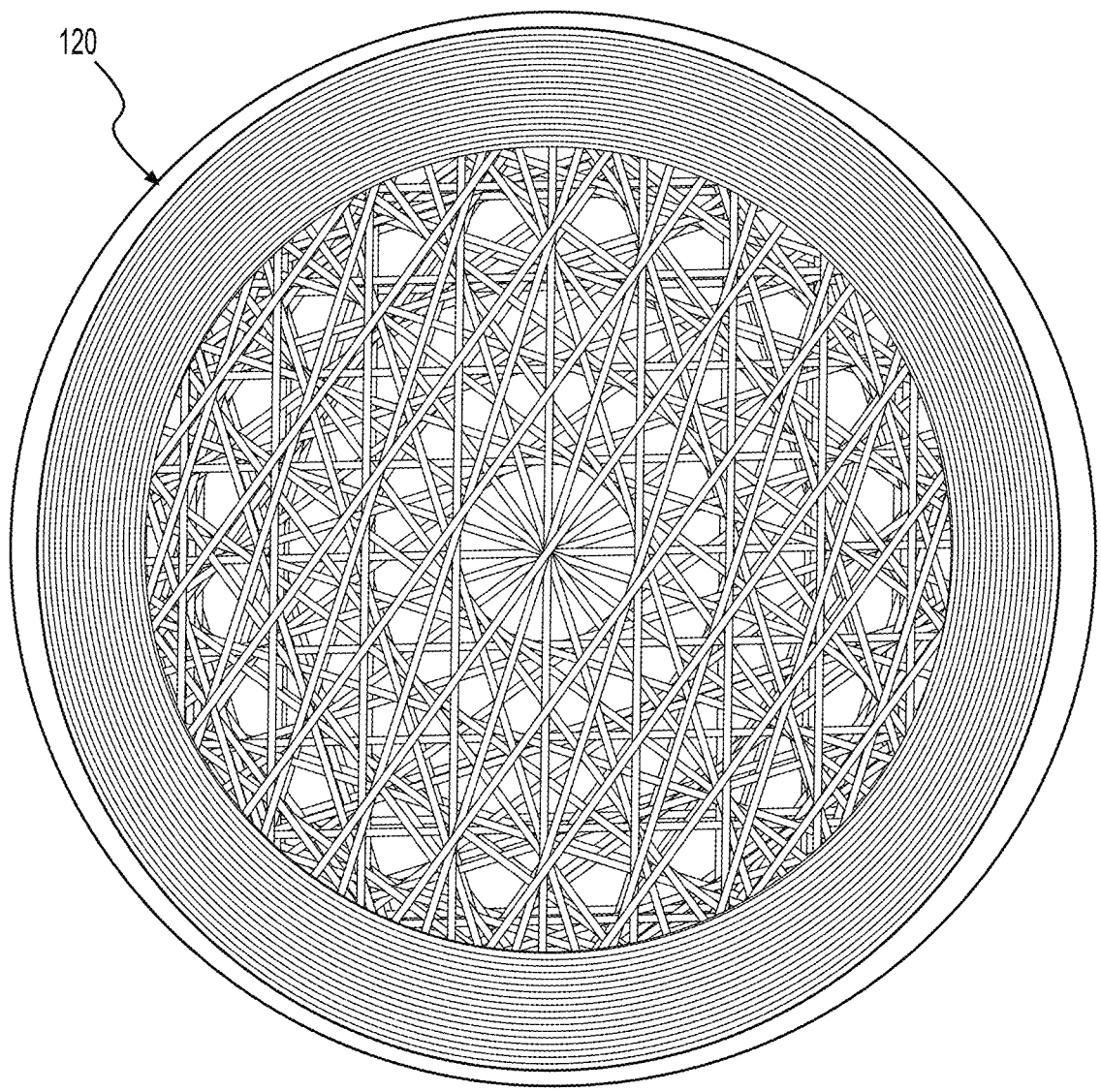
FIG. 6A is a top view of a cross section along the mid plane of a breast implant 120 in accordance with one embodiment of the invention. The breast implant scaffold 120 is shown having stacking layers of parallel filaments with each subsequent layer of filaments crisscrossed with the prior layer of filaments, at an 18-degree angle, to form a porous infill pattern. Every eleventh layer of filaments is oriented in the same direction. The implant has an outer shell prepared from concentric stacks of a single filament at the periphery of the implant that enclose the stacked layers of parallel filaments.
Figure 6B:
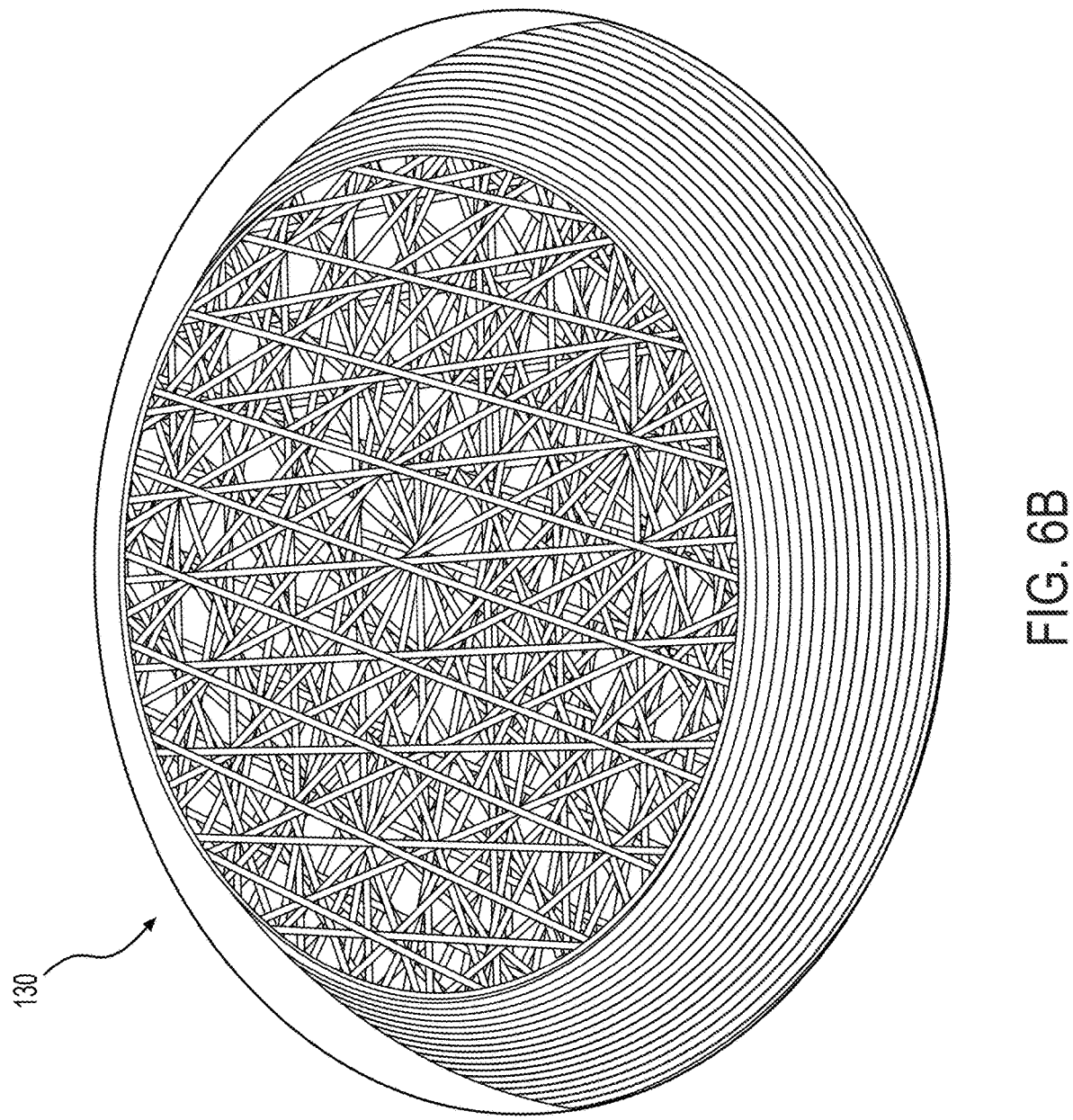
FIG. 6B is a partial isometric view of the cross section along the mid plane of a breast implant 130 shown in FIG. 6A prepared by stacking layers of parallel filaments with each subsequent layer of filaments crisscrossed with the prior layer of filaments, at an 18-degree angle, to form a porous infill pattern. Every eleventh layer of filaments is oriented in the same direction. The implant has an outer shell prepared from concentric stacks of a single filament at the periphery of the implant that enclose the stacked layers of parallel filaments.

FIG. 6A shows a top view of a breast implant 120 formed by stacking layers of parallel filaments together with each successive layer of parallel filaments offset or angled from the prior layer of filaments by 18 degrees. In this example, every eleventh layer of filaments has the same alignment. An alternative isometric view of the same implant shown in FIG. 6A is shown in FIG. 6B as breast implant 130. FIG. 6B clearly shows the stacked layers of parallel filaments.

The breast implant of FIGS. 2A-6A and 2B-6B are formed with shells prepared from a stack of concentric filaments at the periphery of the implant's scaffold enclosing the successive layers of parallel filaments.

The implant may further comprise one or more openings for insertion of a tissue mass. The tissue mass may be a vascular pedicle. In some embodiments, there may be an opening on the back area of the implant for insertion of a tissue mass. The opening may extend partly into the implant, or may extend from the back area to the front area of the implant as shown by opening 7 in FIG. 1A. The implant may comprise an opening on the front bottom 4, front top 5 or front intermediate-region 6 of the implant. These openings may extend partly into the implant, or all the way through the implant. Opening 8 in FIG. 1A is an example of a medial to lateral opening in an implant that is designed for insertion of a tissue mass such as a vascular graft.

An alternative top view of a medial to lateral opening 21 for insertion of a tissue mass is shown in FIG. 1C.

Figure 9:
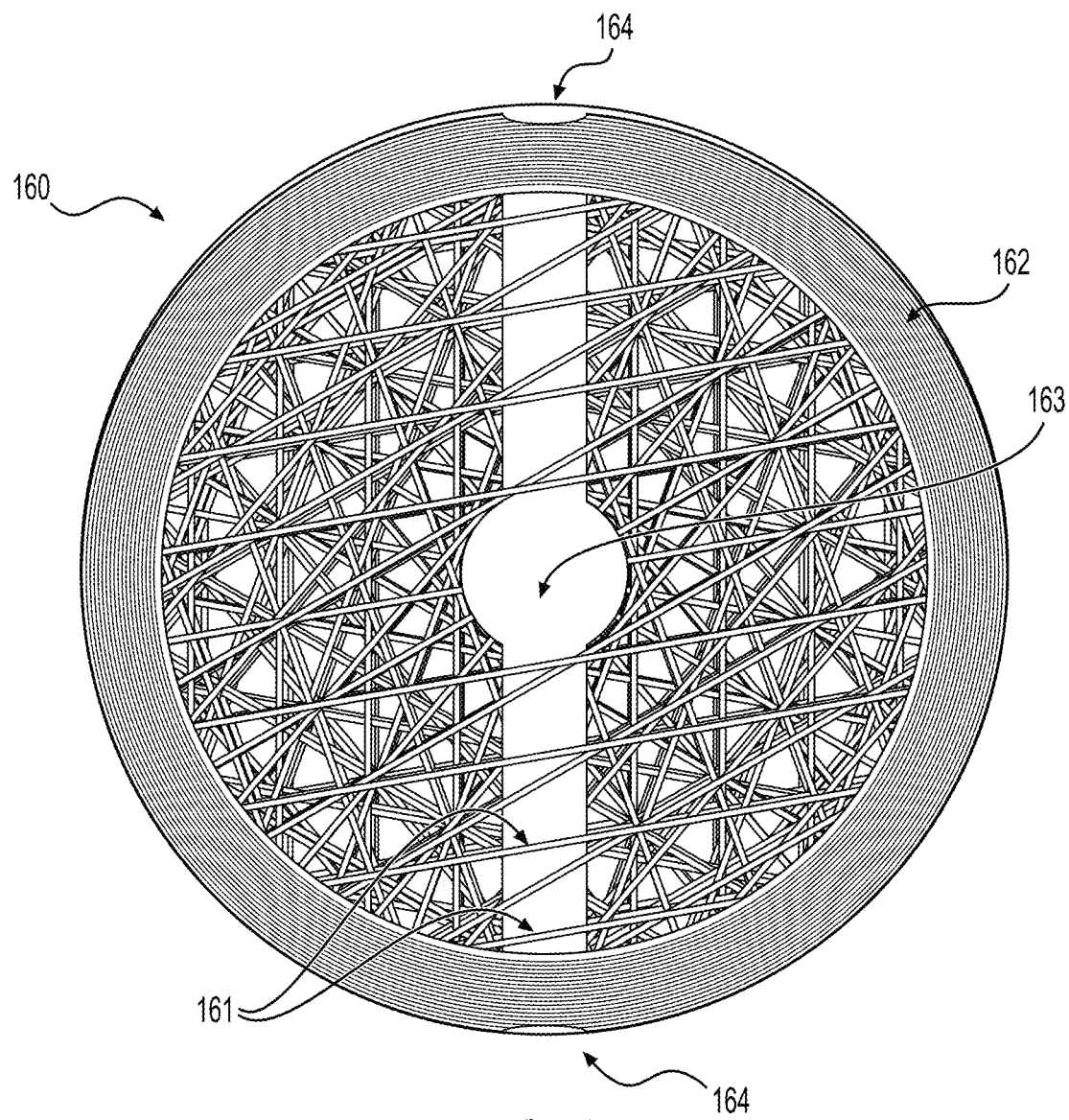
FIG. 9 is a top view of a cross section along the mid plane of a breast implant 160, prepared by stacking layers of parallel filaments 161 with each subsequent layer of filaments crisscrossed with the prior layer of filaments to form a porous infill pattern. The implant has an outer shell 162 prepared from concentric stacks of a single filament at the periphery of the implant that enclose the stacked layers of parallel filaments. The implant has two openings for insertion of tissue mass. One opening 163 between the back area and front area of the implant, and a second opening 164 running through the implant in a medial to lateral direction.

FIG. 9 shows a further example of a breast implant 160, prepared by stacking layers of parallel filaments 161 with each subsequent layer of filaments crisscrossed with the prior layer of filaments to form a porous infill pattern, and wherein the implant further comprises two openings 163 and 164 for insertion of tissue masses. Opening 163 is formed in the center of the implant between the back and front of the implant scaffold. Opening 164 is formed in a medial to lateral direction through the implant scaffold. The implant 160 further comprises an outer shell 162 prepared from concentric stacks of a single filament at the periphery of the implant that encloses the stacked layers of parallel filaments.

In embodiments, the implant may comprise one or more channels in addition to one or more openings for insertion of a pedicle or other tissue mass. In embodiments, the channels are straight. In embodiments, the channels have a diameter greater than 100 μm. The channels through the scaffold can help facilitate vascularization of the implant and tissue ingrowth.

In embodiments, the scaffold of the implant may further comprise an external shell or coating. In embodiments, the shell has an outer surface and an inner surface that surrounds an interior volume of said shell. The external shell or coating may partially or fully encase the filaments of the implant's scaffold. In embodiments, the thickness of the shell or coating is from 10 μm to 5 mm and/or 100 μm to 1 mm. In embodiments, the shell is formed from concentric stacks of a filament at the periphery of the stacked layers of parallel filaments. In embodiments, the thickness of the shell comprises 2, 3, 4, 5 or more filaments side by side.

In embodiments, the shell or coating is permeable to a needle.

In embodiments, the shell comprises a foam with interconnected pores. In embodiments, the shell is an open cell foam, and/or an open cell foam comprising poly-4-hydroxybutyrate or copolymer thereof or poly(butylene succinate) or copolymer thereof.

In embodiments, the shell comprises collagen, and/or type I collagen. In embodiments, the shell comprises collagen, and is 0.1 to 5 mm and/or 0.5 to 3 mm in thickness.

In embodiments, the implant comprises layers of parallel filaments with at least one layer of parallel filaments angled at 1-60 degrees from another layer of parallel filaments, and wherein the implant further comprises a shell surrounding the layers of parallel filaments. In embodiments, the implant comprises layers of parallel filaments with each layer of parallel filaments angled at 1-60 degrees, and/or at 18, 20, 30, 36, 45 or 60 degrees, from another adjacent layer of parallel filaments, and wherein the implant further comprises a shell surrounding the layers of parallel filaments.

In embodiments, the implant comprises a shell wherein the shell has been heat treated to minimize the roughness of the outer surface of the shell.

In embodiments, the implant comprises a shell, and the shell comprises a coating formed from an absorbable polymer and a water-soluble polymer or solid porogen. In embodiments, the shell comprises poly-4-hydroxybutyrate or copolymer thereof, or poly(butylene succinate) or copolymer thereof, and a water-soluble polymer or solid porogen.

In one embodiment, the implant is prepared using 3D printing to construct the implant's scaffold. 3D Printing of the scaffold is highly desirable since it allows precise control of the shape of the implant's scaffold. Suitable methods for 3D printing include fused filament fabrication, fused pellet deposition, melt extrusion deposition, selective laser melting, printing of slurries and solutions using a coagulation bath, and printing using a binding solution and granules of powder. In some embodiments, the scaffold of the implant may be prepared by melt extrusion deposition.

The breast implants depicted in FIGS. 2-6 can be manufactured by melt extrusion deposition. These implants can be printed with different filling densities and with different angles between the filaments. As described above, in embodiments the infill density of the implant's scaffold is from 1 to 60% and/or from 5 to 25%, the average diameters of the filaments are 50 to 800 μm, 100 to 600 μm, and/or 150 to 550 μm, the distances between the filaments of the implant are between 50 μm and 1 mm, 100 μm and 1 mm, and/or 200 μm and 1 mm, and the angles between the filaments in adjacent layers may range from 0 to 179 degrees, 0 to 90 degrees, and/or 0 to 60 degrees. These parameters may be selected according to the properties desired for the scaffold or implant, including the compression modulus and porosity. For example, the porosity of the scaffold may be decreased by decreasing the infill density if the filament sizes, spacing between filaments, and print pattern are kept constant. As the infill density decreases, the compression modulus also decreases if the filament sizes, spacing between filaments, and print pattern are kept constant. An exemplary infill range for the body of the implant is 1 to 50 and/or 5 to 20%. An exemplary infill range for the shell of the implant is 50 to 100 and/or 80 to 100%.

In a typical procedure, the implant is prepared by melt extrusion deposition of a composition comprising an absorbable polymer or blend thereof.

The absorbable polymer or blend may be dried prior to printing to avoid a substantial loss of intrinsic viscosity. In some embodiments, the polymer or blend may be dried so that the moisture content of the composition to be printed is no greater than 0.5 wt. % as measured gravimetrically, and/or no greater than 0.05 wt. %. The polymer or blend may be dried in vacuo. In some embodiments, the polymer or blend may be dried in a vacuum chamber under a vacuum of at least 10 mbar and/or at least 0.8 mbar, to a moisture content of less than 0.03% by weight. Elevated temperatures below the melting point of the polymer may also be used in the drying process. Alternatively, the polymer may be dried by extraction into a solvent and re-precipitation of the polymer, or with the use of desiccants. The moisture content of the polymer or blend may be determined using a VaporPro Moisture Analyzer from Arizona Instruments, or similar instrument.

In an embodiment, the implant may be formed by melt extrusion deposition of poly-4-hydroxybutyrate (P4HB). P4HB polymer (Mw of 100-600 kDa) is pelletized prior to melt extrusion deposition, and dried as described above. A suitable 3D printer for printing the implant's scaffold is an Arburg Freeformer 3D printer. P4HB pellets may be 3D printed to form the scaffold of a breast implant (as shown in the examples of FIGS. 2-6) using, for example, the printing parameters shown in Table 1 and the Arburg Freeformer 3D printer, and a 3D CAM (Computer Aided Design Model) for the implant's scaffold. The average diameters of the 3D filaments that are printed from the P4HB polymer are selected based upon the properties of the implant desired, including the implant's compression modulus, and porosity or fill density (i.e. the number of 3D printed filaments per mm between the contours of the 3D printed device). In some embodiments, the average filament diameters or widths may be 50 to 800 μm, 100 to 600 μm, and/or 150 to 550 μm.

TABLE 1

Parameters for Melt Extrusion Deposition Printing of P4HB Breast Implant Scaffolds

| | |
|---|---|
| Print head temp (° C.) | 185 |
| Barrel zone 2 (° C.) | 135 |
| Barrel zone 1 (° C.) | 100 |
| Build chamber temp (° C.) | 10-15° C. |
| Screw speed (m/min) | 4 |
| Back pressure (MPa) | 50 |
| Recovery stroke (mm) | 6 |
| Deco speed (mm/s) | 2 |
| Deco stroke (mm) | 4 |
| Discharge nr (%): | 55-75 |
| In Filling density Shell (%) | 30-100 |
| In Filling density Body (%) | 1-50 |
| Drop ratio | 1-1.4 |

In another embodiment, the parameters shown in Table 2 may be used to 3D print the implant using a composition comprising poly(butylene succinate) or copolymer thereof.

TABLE 2

Parameters for Melt Extrusion Deposition Printing of PBS Breast Implant Scaffolds

| | |
|---|---|
| Print head temp (° C.) | 190-200 |
| Barrel zone 2 (° C.) | 150 |
| Barrel zone 1 (° C.) | 110 |
| Build chamber temp (° C.) | 50 |
| Screw speed (m/min) | 4 |
| Back pressure (MPa) | 50 |
| Recovery stroke (mm) | 6 |
| Deco speed (mm/s) | 2 |
| Deco stroke (mm) | 4 |
| Discharge nr (%): | 60-75 |
| In Filling density Shell (%) | 30-100 |
| In Filling density Body (%) | 1-50 |
| Drop ratio | 1-1.4 |

C. Properties of the Implant

In an embodiment, the mechanical properties of the scaffold are designed so that the mechanical properties of the implant approximate the mechanical properties of breast tissue.

In one embodiment, the compressive modulus of the implant is 0.1 kPa to 10 MPa, 0.3 kPa to 1 MPa, and/or 3 kPa to 200 kPa. In embodiments, the compressive modulus of the implant allows the implant to be compressed when a compressive force is applied, but recover from compression when the compressive force is removed.

In another embodiment, the implant has a compressive modulus that is ±50% of the compressive modulus of breast tissue. In other embodiments, the implant has a compressive modulus that is ±50% and/or ±25% of the compressive modulus of glandular tissue, adipose tissue, skin, pectoralis fascia, or breast tissue.

In embodiments, the planes of filaments present in the scaffold of the breast implant are formed from a polymeric composition. The polymeric composition may have one or more of the following properties: (i) an elongation at break greater than 100%; (ii) an elongation at break greater than 200%; (iii) a melting temperature of 60° C. or higher, (iv) a melting temperature higher than 100° C., (v) a glass transition temperature of less than 0° C., (vi) a glass transition temperature between −55° C. and 0° C., (vii) a tensile modulus less than 300 MPa, and (viii) a tensile strength higher than 25 MPa.

In embodiments, the planes of filaments present in the scaffold of the breast implant have one or more of the following properties: (i) breaking load of 0.1 to 200 N, 1 to 100 N, or 2 to 50 N; (ii) elongation at break of 10% to 1,000%, 25% to 500%, and/or greater than 100% or 200%, and (iii) elastic modulus of 0.05 to 1,000 MPa and/or 0.1 to 200 MPa.

In embodiments, the scaffold of the implant may have anisotropic properties. That is, the scaffold may have different properties in different directions. For example, the scaffold may have a first compressive modulus in one direction, and a second different compressive modulus in a second direction. In embodiments, the scaffolds of the breast implants may have different properties in the direction from the font top to the front bottom of the implant versus the properties of the implant measured from a lateral to medial direction when implanted in the breast.

In order to allow tissue in-growth into the scaffold of the implant, the scaffold should have a strength retention long enough to permit cells and blood vessels to invade the implant's scaffold and proliferate. In embodiments, the scaffold of the implant has a strength retention of at least 25% at 2 weeks, at least 50% at 2 weeks, and/or at least 50% at 4 weeks. In other embodiments, the scaffold of the implant is designed to support mechanical forces acting on the implant, and to allow a steady transition of mechanical forces from the scaffold to regenerated host tissues. In particular, the scaffold of the implant is designed to support mechanical forces acting on the implant, and to allow a steady transition of mechanical forces from the scaffold to new host tissues.

D. Other Features of the Implants

The implants or scaffolds of the implants may be trimmed or cut with scissors, blades, other sharp cutting instruments, or thermal knives in order to provide the desired implant or scaffold shapes. The implants or scaffolds can also be cut into the desired shapes using laser-cutting techniques. This can be particularly advantageous in shaping filament-based implants because the technique is versatile, and importantly can provide shaped implants and scaffolds without sharp edges.

In embodiments, the implants may further comprise pillars to reinforce the implants or to facilitate implantation. The pillars may, for example, help to reshape the implant following implantation. In some embodiments, the pillars may be incorporated into the scaffold structures in order to reinforce the implants or facilitate implantation of the implant. The pillars may be incorporated into the implants by any suitable method, including fusion, molding, weaving, knitting, or printing. In some embodiments, pillars are incorporated by fusing absorbable polymeric fibers or struts to the scaffold of the implant. In embodiments, the pillar may have diameters or widths ranging from 0.1 to 5 mm and/or 0.5 to 3 mm. The absorbable polymeric fibers or struts may be oriented or unoriented, unoriented and/or unoriented poly-4-hydroxybutyrate fibers or struts, or unoriented poly(butylene succinate) fibers or struts. In another embodiment, flexible pillars may be printed directly onto the scaffold of the implant, or incorporated into the scaffold during printing of the scaffold.

The implants may comprise retainers, such as barbs or tacks, so that the implant can be anchored in the body without the use of sutures. The implants may contain the retainers in the outlying borders of the implant or scaffold structure of the implant. In embodiments, the retainers may be located on the implant to allow the implant to be anchored to the chest wall.

The implant may comprise suture tabs so that the implants can be anchored in the body using for example sutures and/or staples. The number of tabs may vary. In one embodiment, the number of tabs will depend upon the load exerted on the implant. A larger number of tabs may be desirable when the implant is heavier or has a larger volume. In embodiments, the implant comprises 1, 2, 3, 4, 5, 6, 7, 8, 9, 10, 11, 12, 13, 14, 15, 16, 17, 18, 19, 20 tabs or more. In embodiments, the implant may contain 4 or more tabs, such as 4-12 tabs, in order to anchor the breast implant to the chest wall. The dimensions of the tabs may be from 0.5 cm×0.5 cm to 5 cm×4 cm and/or 2 cm×2.5 cm. The tabs attached to the implant must have sufficient strength retention in vivo to resist mechanical loads, and to allow sufficient in-growth of tissue into the implant in order to prevent subsequent movement of the implant after implantation. In some embodiments, the suture pullout strength of the tabs attached to the implant, is greater than 10 N and/or greater than 20 N.

Examples of various types of pillars, tabs and barbs are shown and described in US Patent Publication No. 20190247180, filed Jan. 30, 2019, and entitled "FULL CONTOUR BREAST IMPLANT" incorporated herein by reference in its entirety.

E. Implant Coatings and Fillings

The scaffold of the implant comprises a network wherein there is a continuous path through the scaffold which encourages and allows tissue ingrowth into the scaffold structure. The continuous path also allows the entire scaffold structure to be coated with one or more of the following: bioactive agents, collagen, recombinant collagen, hyaluronic acid or derivative thereof, additives, cells and tissue, including fat and fat cells.

Scaffolds with low infill densities, for example, less than 60%, or 5-25%, may provide sufficient void space that may be occupied, for example, by cells, tissues, collagen, and bioactive agents, including fat, lipoaspirate, adipose cells, fibroblast cells, and stem cells. In one embodiment, 25% to 100% and/or 75% to 100% of the void space of the implant's scaffold is filled with one or more of the following: cells, tissues, collagen, and bioactive agents, including fat, lipoaspirate, adipose cells, fibroblast cells, and stem cells.

The cells and other compositions, such as collagen, recombinant collagen, hyaluronic acid or derivative thereof, and other bioactive agents, may be coated on the scaffold prior to implantation, after implantation, or both before and after implantation.

In embodiments, the implants are fabricated with coatings and/or some or all of the scaffold is used as a carrier. For example, the scaffold may be fabricated by populating some or all of the void space of the scaffold with one or more of the following: cells and tissue, including autograft, allograft or xenograft tissue and cells, and vascularized pedicle. Examples of cells that can be inserted into the void spaces of the implant's scaffold, and coated on the surfaces of the scaffold, include adipose cells, fibroblast cells, and stem cells. In some embodiments, autologous fat, fat lipoaspirate, or injectable fat, is coated on the implant's scaffold and/or inserted into void space of the implant's scaffold. In some embodiments, a vascularized pedicle may be inserted into void space of the implant's scaffold. In some embodiments, the implant's scaffold can be coated or partially or fully filled with one or more bioactive agents. Bioactive agents that may be coated on the implant's scaffold or used to partially or completely fill the implant's scaffold include collagen (including recombinant collagen) and hyaluronic acid or derivative thereof. In other embodiments, the implant's scaffold may be coated with one or more antibiotics.

Any suitable method can be used to coat the implant's scaffold and fill its void space with cells, tissue, bioactive agents and other additives. In embodiments, the implant's scaffold is filled or coated with cells, tissue, bioactive agents and other additives by injection, spraying, or dip-coating. Collagen may be applied to the implant's scaffold by coating and freeze-drying. In some embodiments, the implant's scaffold may be coated or partially or completely filled with cells, tissue, bioactive agents and/or other additives by injection using needles that can be inserted into the scaffold of the implant without significantly damaging the scaffold. In one embodiment, the needles used for injection of cells, tissue, fat, fat lipoaspirate, bioactive agents, collagen, recombinant collagen, hyaluronic acid or derivative thereof, and other additives have outer diameters between 0.5 mm and 5 mm.

IV. Methods for Implanting the Implants

In embodiments, the implant is implanted into the body. In some embodiments, the implant may be implanted into a site of reconstruction, remodeling, repair, and/or regeneration. In some embodiments, the implant is implanted in the breast of a patient. In some embodiments, connective tissue and/or vasculature will invade the scaffold of the implant after implantation. In some embodiments, the implant comprises absorbable materials, and connective tissue and/or vasculature will also invade the spaces where the absorbable materials have degraded. The pores of the scaffold may be colonized by cells prior to implantation or following implantation, and the pores of the implant's scaffold invaded by tissue, blood vessels or a combination thereof.

The implant's scaffold may be coated or filled with transplantation cells, stem cells, fibroblast cells, adipose cells, and/or tissues prior to implantation, or after implantation. In embodiments, the implant's scaffold is coated or filled with differentiated cells prior to, or subsequent to, implantation. Differentiated cells have a specific form and function. An example is a fat cell. In some embodiments, the implant's scaffold may be populated with cells by injection, before or after implantation, and/or by using needles that do not damage the scaffold of the implant. The implant's scaffold may also be coated or filled with platelets, extracellular adipose matrix proteins, gels, hydrogels, and bioactive agents prior to implantation. In an embodiment, the implant's scaffold may be coated with antibiotic prior to implantation, for example, by dipping the implant in a solution of antibiotic.

The implants may be used to deliver autologous cells and tissue to the patient in the breast. The autologous tissue may be one or more of the following: autologous fat, fat lipoaspirate, injectable fat, adipose cells, fibroblast cells, and stem cells.

The implants may be used to deliver fat tissue into a patient. In some embodiments, autologous fatty tissue is prepared prior to, or following, implantation of the implant, and is injected or otherwise inserted into or coated on the implant's scaffold prior to or following implantation of the implant. The autologous fatty tissue may be prepared by liposuction at a donor site on the patient's body. After centrifugation, the lipid phase containing adipocytes is then separated from blood elements, and combined with the implant's scaffold prior to implantation, or injected, or otherwise inserted into the implant's scaffold following implantation. In an embodiment, the implant's scaffold is injected with, or filled with, a volume of lipoaspirate that represents 1% to 50% and/or 1% to 20% of the total volume of the scaffold.

In another embodiment, lipoaspirate fatty tissue taken from the patient may be mixed with a biological or synthetic matrix, such as very small fibers or particles, prior to adding the lipoaspirate to the implant's scaffold. In this embodiment, the added matrix serves to hold or bind micro-globules of fat, and disperse and retain them within the scaffold of the implant. In some embodiments, the use of added matrix can help to prevent pooling of fat which could lead to necrosis, and/or help to increase vascularization of the implant.

In another embodiment, a vascular pedicle or other tissue mass is harvested from the patient, and inserted into the implant. The pedicle or other tissue mass may be inserted into the implant prior to implantation of the implant, and then the implant with the pedicle or other tissue mass implanted in the patient, or the pedicle or other tissue mass may be inserted into the implant after the implant has been implanted in the patient.

In an embodiment, an implant is implanted and fixated in both breasts. In embodiments, the implants are implanted in patients during mastopexy and augmentation procedures, including revision procedures. In some embodiments, the implant is implanted in a patient that has undergone a: (i) mastectomy, (ii) breast lift and has need of augmentation, (iii) breast reduction and needs support, lift or remodeling of the reduced breast, or (iv) previous silicone or saline breast implant surgery and desires the silicone or saline implant to be removed and that a subsequent reconstruction of the breast will provide a fuller or large sized breast. The implant may also be implanted in a breast surgery patient to increase the projection of the breast away from the chest, and optionally additional fat graft volume added to the implant after implantation to increase the projection. Additional fat graft volume may be added to the implant immediately after implantation of the implant, but may also be added at follow up visits. For example, additional fat graft volume may be added to the implant on one or more occasions that are days, weeks, or months following the implantation of the implant. The procedures described herein can also be performed with removal of breast tissue, resection and redistribution of breast tissue.

In an embodiment, a method of implantation of the implant in the breast comprises at least the steps of: (i) making at least one incision to gain access to the breast tissue of the patient, (ii) separating the skin and subcutaneous fascia from the breast mound of the breast, (iii) positioning the implant on the breast mound of the breast, (iv) securing the implant to the tissue surrounding the breast mound of the breast, and (v) closing the incisions in the breast. In some embodiments, this method further comprises one or more of the following steps: (a) preparing a sample of lipoaspirate, and coating or filling the implant with the sample prior to implantation of the implant, (b) preparing a sample of lipoaspirate, and coating or filling the implant with the sample after implantation of the implant, (e.g., by injecting the sample into the implant), (c) inserting a vascular pedicle into the implant prior to, or after, implantation of the implant, and (d) suturing or stapling the implant in place. In some embodiments, the implant is implanted in a sub-glandular, sub-pectoral or pre-pectoral position. In embodiments, the implant may be sutured to the tissue surrounding the breast mound, and/or to the fascia surrounding the pectoral muscle underlying the breast mound. In another embodiment, the implant comprises tabs, and the tabs are sutured to the tissue surrounding the breast mound.

The implant's scaffold may also be coated or filled with cells and tissues other than fat grafts prior to, or subsequent to, implantation, as well as with cytokines, platelets and extracellular adipose matrix proteins. For example, the implant's scaffold may be coated or filled with cartilage or dermal grafts. The implant's scaffold may also be coated or filled with other tissue cells, such as stem cells genetically altered to contain genes for treatment of patient illnesses.

In an embodiment, the implant has properties that allows it to be delivered by minimally invasive means through a small incision. The implant may, for example, be designed so that it can be rolled, folded or compressed to allow delivery through a small incision. This minimally invasive approach can reduce patient morbidity, scarring and the chance of infection. In some embodiments, the implant has a three-dimensional shape and shape memory properties that allow it to assume its original three-dimensional shape unaided after it has been delivered through an incision and into an appropriately sized dissected tissue plane. For example, the implant may be temporarily deformed by rolling it up into a small diameter cylindrical shape, delivered using an inserter, and then allowed to resume its original three-dimensional shape unaided in vivo.

EXAMPLES

The present invention will be further understood by reference to the following non-limiting example.

Example 1: Breast Implant Scaffold With Porous Scaffold of Stacked Layers of Parallel Filaments Surrounded by Shell of Concentric Filaments The breast implant scaffold shown in FIGS. 2A, 2B was prepared as described herein. Pellets of P4HB (Tepha, Inc., Mw 480 kDa) were loaded into the hopper of a melt extrusion deposition (MED) based 3D printer comprising a horizontal extruder feeding into a vertical extruder fitted with a vertical plunger, and a movable stage. An exemplary process for using melt extrusion to eject a series of droplets on demand in preparing an implant is described in Patent Publication No. 2019/0375149, filed Jun. 11, 2019, and entitled "METHODS FOR 3D PRINTING OF POLY-4 HYDROXYBUTYRATE AND COPOLYMERS", incorporated herein by reference in its entirety.

Pellets had an average diameter of 3.5 mm, moisture content of less than 100 ppm, and were kept dry in the hopper using a purge of air dried through a silica bed. The temperature profile of the horizontal extruder was set to 30° C. in the build chamber; 100° C. in the first transition zone, 130° C. in second transition zone; and 230° C. in the extrusion zone. The residence time of the polymer in the MED horizontal extruder was 22 min/cm$^3$. The back pressure was set to 50 bars (5 MPa). The diameter of the nozzle orifice of the vertical extruder was 0.2 mm and the drop printing frequency was 50 drops/sec at the edge of the printed construct (shell) and 240 drops/sec for the in-fill.

The 3D printer was loaded with an STL file to print the open porous scaffold structure of the implant shown in FIGS. 2A, 2B.

The resulting structure had a dome shape with a base diameter of 12 cm, and a projection of 5.5 cm (height from base to apex). The structure inside the shell of the implant was formed with a completely interconnected porous architecture with open porosity.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:

1. A breast implant comprising a porous three-dimensional scaffold, wherein the implant comprises a back area for placement on the chest wall of a patient, a front area opposite the back area, the front area comprising a front bottom for placement in the lower pole of the breast, a front top for placement in the upper pole of the breast, and a front intermediate-region for placement under the skin of the patient, wherein the implant has a compressive modulus of 0.1 kPa to 10 MPa, wherein the scaffold comprises at least two adjacent parallel planes of filaments bonded to each other, and wherein the filaments in each plane extend in the same direction.

2. The implant of claim 1, wherein the front bottom of the implant has a convex exterior surface.

3. The implant of claim 1, wherein the parallel planes of filaments are formed with a polymer, and wherein the polymer has one or more of the following properties: (i) an elongation at break greater than 100%; (ii) an elongation at break greater than 200%; (iii) a melting temperature of 60° C. or higher, (iv) a melting temperature higher than 100° C., (v) a glass transition temperature of less than 0° C., (vi) a glass transition temperature between −55° C. and 0° C., (vii) a tensile modulus less than 300 MPa, and (viii) a tensile strength higher than 25 MPa.

4. The implant of claim 1, wherein the implant has a loss modulus of 0.3 to 100 kPa.

5. The implant of claim 2, wherein the convex exterior surface approximates the anatomical feature of the lower pole of a breast.

6. The implant of claim 1, wherein at least two parallel planes of filaments have the same orientation in adjacent planes or nonadjacent planes.

7. The implant of claim 1, wherein a first parallel plane of filaments is organized in a first geometrical orientation, and a second parallel plane of filaments is arranged in a second geometrical orientation such that a porous scaffold of crisscrossed filaments is formed through the scaffold.

8. The implant of claim 7, wherein the scaffold further comprises a third parallel plane of filaments, and the filaments in the first, second and third parallel planes form pores with a triangular shape.

9. The implant of claim 1, wherein an angle between the filaments in the parallel planes is selected from one of the following: between 1 and 120 degrees, or 18, 20, 30, 36, 45 or 60 degrees.

10. The implant of claim 1, wherein the scaffold further comprises a plurality of hollow channels.

11. The implant of claim 10, wherein the channels have a diameter greater than 100 microns.

12. The implant of claim 1, wherein the filaments have one or more of the following properties: an average diameter or average width of 10 μm to 5 mm, a breaking load of 0.1 to 200 N, an elongation at break of 10 to 1,000% or 25 to 500%, and elastic modulus of 0.05 to 1,000 MPa or 0.1 to 200 MPa.

13. The implant of claim 1, wherein the at least two parallel planes of filaments are bonded together by 3D printing the filaments.

14. The implant of claim 1, wherein an infill density of filaments in the scaffold is selected from one of the following: between 1% and 60%, or between 5% and 25%.

15. The implant of claim 1, wherein the implant further comprises a shell or coating at least partly surrounding the parallel planes of filaments.

16. The implant of claim 15, wherein the shell has an outer surface and an inner surface that surrounds an interior volume of said shell.

17. The implant of claim 15, wherein the shell comprises a stack of concentric filaments.

18. The implant of claim 1, wherein the implant is absorbable.

19. The implant of claim 1, wherein the compressive modulus decreases, within 2 years from being implanted, to less than or equal to 200 kPa.

20. The implant of claim 1, wherein the implant is configured to recover at least 50%, 70%, or 90% of its original volume upon application and subsequent removal of a compressive force.

21. The implant of claim 1, wherein the implant has a compression resilience between 1-80%.

22. A method of manufacturing a breast implant comprising a porous three-dimensional scaffold, wherein the implant comprises a back area for placement on the chest wall of a patient, a front area opposite the back area, the front area comprising a front bottom for placement in the lower pole of the breast, a front top for placement in the upper pole of the breast, and a front intermediate-region for placement under the skin of the patient, wherein the implant has a compressive modulus of 0.1 kPa to 10 MPa, and wherein the scaffold comprises at least two adjacent parallel planes of filaments bonded to each other with the filaments in each plane extending in the same direction, wherein the method comprises forming a scaffold by one of the following (i) forming at least two parallel planes of filaments from a polymeric composition by 3D printing of the filaments, and (ii) forming at least two parallel planes of filaments from a polymeric composition by melt extrusion deposition printing.

23. The method of claim 22, wherein the front bottom of the implant has a convex exterior surface.

24. The method of claim 22, wherein the polymeric composition is selected from a polymer or copolymer comprising, or prepared from, one or more of the following monomers: glycolide, lactide, glycolic acid, lactic acid, 1,4-dioxanone, trimethylene carbonate, 3-hydroxybutyric acid, 3-hydroxybutyrate, 3-hydroxyhexanoate, 3-hydroxyoctanoate, 4-hydroxybutyric acid, 4-hydroxybutyrate, ε-caprolactone, 1,4-butanediol, 1,3-propane diol, ethylene glycol, glutaric acid, malic acid, malonic acid, oxalic acid, succinic aid, and adipic acid, or wherein the polymeric composition comprises poly-4-hydroxybutyrate or copolymer thereof, or poly(butylene succinate) or copolymer thereof.

25. The method of claim 22, wherein the filaments are formed with a polymer, and wherein the polymer has one or more of the following properties: (i) an elongation at break greater than 100%; (ii) an elongation at break greater than 200%; (iii) a melting temperature of 60° C. or higher, (iv) a melting temperature higher than 100° C., (v) a glass transition temperature of less than 0° C., (vi) a glass transition temperature between −55° C. and 0° C., (vii) a tensile modulus less than 300 MPa, and (viii) a tensile strength higher than 25 MPa.

26. The method of claim 22, wherein the filaments have one or more of the following properties: (i) average diameter or average width of 10 μm to 5 mm, (ii) breaking load of 0.1 to 200 N, 1 to 100 N, or 2 to 50 N, (iii) an elongation at break of 10 to 1,000% or 25 to 500%, or greater than 100% or 200%, (iii) elastic modulus of 0.05 to 1,000 MPa or 0.1 to 200 MPa.

27. The method of claim 22, wherein the scaffold has a loss modulus of 0.1 kPa to 5 MPa.

28. The method of claim 22, further comprising:
compressing the implant with a compressive force; and
removing the compressive force from the implant, wherein the implant is configured to recover at least 50%, 70%, or 90% of its original volume after removal of the compressive force.

29. The method of claim 22, wherein the implant has a compression resilience between 1-80%.

* * * * *

UNITED STATES PATENT AND TRADEMARK OFFICE
CERTIFICATE OF CORRECTION

PATENT NO. : 12,156,802 B2
APPLICATION NO. : 17/689538
DATED : December 3, 2024
INVENTOR(S) : Skander Limem et al.

It is certified that error appears in the above-identified patent and that said Letters Patent is hereby corrected as shown below:

In the Specification

At Column 22, Lines 62-63 "where a is a multiple of 2, 3 or 5" should read --where $\alpha$ is a multiple of 2, 3 or 5--

Signed and Sealed this
Fourth Day of February, 2025

Coke Morgan Stewart
*Acting Director of the United States Patent and Trademark Office*